US009993362B2

(12) United States Patent
Costello et al.

(10) Patent No.: US 9,993,362 B2
(45) Date of Patent: Jun. 12, 2018

(54) ADJUSTABLE KNEE BRACE

(71) Applicant: DeRoyal Global Healthcare Solutions Limited, Dublin (IE)

(72) Inventors: Mark Costello, County Mayo (IE); Charles J. French, III, Lenoir City, TN (US); Gregory S. Hodge, Knoxville, TN (US); Brian Ledwith, County Galway (IE); Adrian McDermott, County Galway (IE); Kathleen L. Parker, Knoxville, TN (US); Nephi Zufelt, Peyton, CO (US)

(73) Assignee: DeRoyal Global Healthcare Solutions Limited (IE)

( * ) Notice: Subject to any disclaimer, the term of this patent is extended or adjusted under 35 U.S.C. 154(b) by 387 days.

(21) Appl. No.: 14/788,010

(22) Filed: Jun. 30, 2015

(65) Prior Publication Data

US 2017/0000639 A1  Jan. 5, 2017

(51) Int. Cl.
*A61F 5/01* (2006.01)

(52) U.S. Cl.
CPC .......... *A61F 5/0125* (2013.01); *A61F 5/0123* (2013.01); *A61F 2005/0158* (2013.01);
(Continued)

(58) Field of Classification Search
CPC .................. A61F 5/0123; A61F 5/0125; A61F 2005/0158; A61F 2005/0165;
(Continued)

(56) References Cited

U.S. PATENT DOCUMENTS 5,025,782 A  6/1991 Salerno
5,138,911 A  8/1992 Lan
(Continued)

OTHER PUBLICATIONS

Deroyal, Transition (KB7000) Knee Brace, Dec. 2007.
DJO Global, DonJoy, The X-Act Rom Knee, 2014.

*Primary Examiner* — Keri J Nelson
(74) *Attorney, Agent, or Firm* — Luedeka Neely Group, PC

(57) ABSTRACT

An adjustable knee brace for fitting a variety of leg sizes and adjustable to limit flexion or extension motion of a knee. The knee brace includes an adjustable length provided by a strut that telescopes within a receiver. A latch assembly mounted on the receiver selectively applies a frictional force to lock the strut member and the receiver against relative telescoping movement. An adjustable range of motion hinge is operatively associated with the telescoping strut. The hinge includes a hinge plate connected to the strut member and having a semi-circular peripheral edge defining a plurality of uniformly spaced apart keys. A range of motion stop is movably positionable relative to the semi-circular peripheral edge and includes a movable latch having teeth. The latch is movable away from the keys to an unlocked position in which the stop is movable relative to the keys, and the movable latch is movable toward and into engagement with the keys to a locked position in which the range of motion stop is not movable relative to the keys. The range of motion stop defines a limit of rotational movement of the range of motion hinge to limit extension or flexion motion of the knee.

9 Claims, 22 Drawing Sheets

(52) U.S. Cl.
CPC ............... *A61F 2005/0165* (2013.01); *A61F 2005/0167* (2013.01); *A61F 2005/0174* (2013.01)

(58) Field of Classification Search
CPC ...... A61F 2005/0167; A61F 2005/0172; A61F 2005/0174
USPC .............................................. 602/16, 23, 26
See application file for complete search history.

(56) References Cited

U.S. PATENT DOCUMENTS

| | | |
|---|---|---|
| 5,242,378 A | 9/1993 | Baker |
| 5,472,410 A | 12/1995 | Hamersly |
| 5,980,435 A | 11/1999 | Joutras et al. |
| 5,997,493 A | 12/1999 | Young |
| 6,764,457 B2 | 7/2004 | Hogg |
| 6,981,957 B2 | 1/2006 | Knecht et al. |
| 7,037,287 B2 | 5/2006 | Cormier et al. |
| 7,059,329 B2 | 6/2006 | Mason et al. |
| 7,097,627 B2 | 8/2006 | Enzerink et al. |
| 7,117,569 B2 | 10/2006 | Bledsoe |
| 7,128,723 B2 | 10/2006 | Doty et al. |
| 7,431,708 B2 | 10/2008 | Sreeramagiri |
| 7,485,103 B2 | 2/2009 | Mason et al. |
| 7,833,181 B2 | 11/2010 | Cormier et al. |
| 8,016,781 B2 | 9/2011 | Ongimundarson et al. |
| 8,172,781 B2 | 5/2012 | Oddou et al. |
| 8,277,403 B2 | 10/2012 | Ceriani et al. |
| 8,945,031 B2 | 2/2015 | Cardinall |
| 9,132,026 B2 | 9/2015 | Bledsoe et al. |
| 2006/0206045 A1 | 9/2006 | Townsend et al. |
| 2007/0270976 A1 | 11/2007 | DeHarde et al. |
| 2009/0308400 A1 | 12/2009 | Wilson et al. |
| 2010/0174220 A1 | 7/2010 | Fout et al. |
| 2011/0288611 A1* | 11/2011 | Lunau ............... A61B 5/6828 607/51 |
| 2014/0207038 A1 | 7/2014 | Santaniello et al. |
| 2014/0222166 A1 | 8/2014 | Olafsson et al. |

* cited by examiner

ADJUSTABLE KNEE BRACE

FIELD

This present disclosure relates to adjustable knee braces. More particularly, the disclosure relates to an adjustable postoperative knee brace having telescoping struts and a range of motion hinge that facilitate fitting of the brace and desired adjustment of flexion and extension settings of the brace.

BACKGROUND

Improvement is desired in the construction of adjustable postoperative knee braces. These braces are used in the post-surgery setting to help provide knee immobilization or range of motion limitations as prescribed by a medical practitioner. Such knee braces are typically used post-injury, post-operatively or throughout rehabilitation.

The telescoping function in these braces provides adjustability for these braces to fit different sized legs. A range of motion mechanism enables incremental flexion or extension of the knee, or full locking of the position of the knee.

The present disclosure relates to adjustable knee braces of improved construction. The knee brace includes a telescoping strut structure and range of motion hinge structure that is easier to use and facilitates desired adjustment of flexion and extension settings of the knee brace, and locking of the knee brace.

SUMMARY

In one aspect, the disclosure advantageously provides a telescoping strut for an adjustable knee brace. The telescoping strut includes a strut member, a receiver configured to receive the strut member and telescopically positionable relative to the strut member, and a latch assembly mounted on the receiver.

The latch assembly includes a cam base having a cam surface adjacent a portion of the strut member received by the receiver and a pivot member pivotable mounted on the receiver for pivotal movement relative to the cam base.

The pivot member has an engagement surface positioned to contact the cam surface of the cam base such that pivoting of the pivot member in one direction relative to the cam base selectively bears the cam base towards the strut member to apply a frictional force to lock the strut member and the receiver against relative telescoping movement. Pivoting the pivot member in an opposite direction removes the frictional force to unlock the strut member and the receiver and enable relative telescoping movement.

In another aspect, the disclosure provides an adjustable range of motion hinge for a knee brace limit flexion or extension motion of a knee.

The hinge includes a hinge plate having a semi-circular peripheral edge defining a plurality of uniformly spaced apart keys. A range of motion stop is movably positionable relative to the semi-circular peripheral edge of the hinge plate. The range of motion stop includes a movable latch having teeth.

The movable latch is movable away from the keys to an unlocked position in which the stop is movable relative to the keys, and the movable latch is movable toward and into engagement with the keys to a locked position in which the range of motion stop is not movable relative to the keys. The range of motion stop defines a limit of rotational movement of the range of motion hinge to limit extension or flexion motion of the knee.

Another aspect of the disclosure relates to an adjustable knee brace for fitting a variety of leg sizes and adjustable to limit flexion or extension motion of a knee.

In one embodiment, the brace includes a telescoping strut provided by a strut member, a receiver configured to receive the strut member and telescopically positionable relative to the strut member, and a latch assembly mounted on the receiver.

The latch assembly includes a cam base having a cam surface adjacent a portion of the strut member received by the receiver and a pivot member pivotable mounted on the receiver for pivotal movement relative to the cam base.

The pivot member has an engagement surface positioned to contact the cam surface of the cam base such that pivoting of the pivot member in one direction relative to the cam base selectively bears the cam base towards the strut member to apply a frictional force to lock the strut member and the receiver against relative telescoping movement. Pivoting the pivot member in an opposite direction removes the frictional force to unlock the strut member and the receiver and enable relative telescoping movement.

A range of motion hinge is operatively associated with the telescoping strut. The range of motion hinge includes a hinge plate connected to the strut member and having a semi-circular peripheral edge defining a plurality of uniformly spaced apart keys.

A range of motion stop is movably positionable relative to the semi-circular peripheral edge, the range of motion stop including a movable latch having teeth. The movable latch is movable away from the keys to an unlocked position in which the stop is movable relative to the keys. The movable latch is movable toward and into engagement with the keys to a locked position in which the range of motion stop is not movable relative to the keys. The range of motion stop defines a limit of rotational movement of the range of motion hinge to limit extension or flexion motion of the knee.

In another embodiment, the brace includes a pair of telescoping struts, each strut having a strut member, a receiver configured to receive the strut member and telescopically positionable relative to the strut member, and a latch assembly mounted on the receiver.

Each latch assembly includes a cam base having a cam surface adjacent a portion of the strut member received by the receiver, and a pivot member pivotable mounted on the receiver for pivotal movement relative to the cam base.

The pivot member has an engagement surface positioned to contact the cam surface of the cam base such that pivoting of the pivot member in one direction relative to the cam base selectively bears the cam base towards the strut member to apply a frictional force to lock the strut member and the receiver against relative telescoping movement, and pivoting the pivot member in an opposite direction removes the frictional force to unlock the strut member and the receiver and enable relative telescoping movement.

The knee brace also includes a range of motion hinge operatively associated with both of the telescoping struts. The hinge includes a pair of mating hinge plates connected to each of the strut members, each hinge plate having a semi-circular peripheral edge defining a plurality of uniformly spaced apart keys, the hinge plates being facing and aligned so that the peripheral edges are aligned and the keys of each hinge plate are aligned to define a first key set and a second key set.

A flexion range of motion stop is movably positionable relative to a first portion of the aligned semi-circular peripheral edges of the hinges, the flexion range of motion stop including a movable latch having teeth.

The movable latch is movable away from the first key set to an unlocked position in which the flexion range of motion stop is movable relative to the first key set, and the movable latch is movable toward and into engagement with the first key set to a locked position in which the flexion range of motion stop is not movable relative to the first key set.

An extension range of motion stop is movably positionable relative to a second portion of the aligned semi-circular peripheral edges of the hinges, the extension range of motion stop including a movable latch having teeth.

The movable latch is movable away from the second key set to an unlocked position in which the extension range of motion stop is movable relative to the second key set, and the movable latch is movable toward and into engagement with the second key set to a locked position in which the extension range of motion stop is not movable relative to the second key set.

The flexion range of motion stop defines a limit of rotational movement of the range of motion hinge to limit flexion motion of the knee and the extension range of motion stop defines a limit of rotational movement of the range of motion hinge to limit extension motion of the knee.

BRIEF DESCRIPTION OF THE DRAWINGS

Further advantages of the disclosure are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
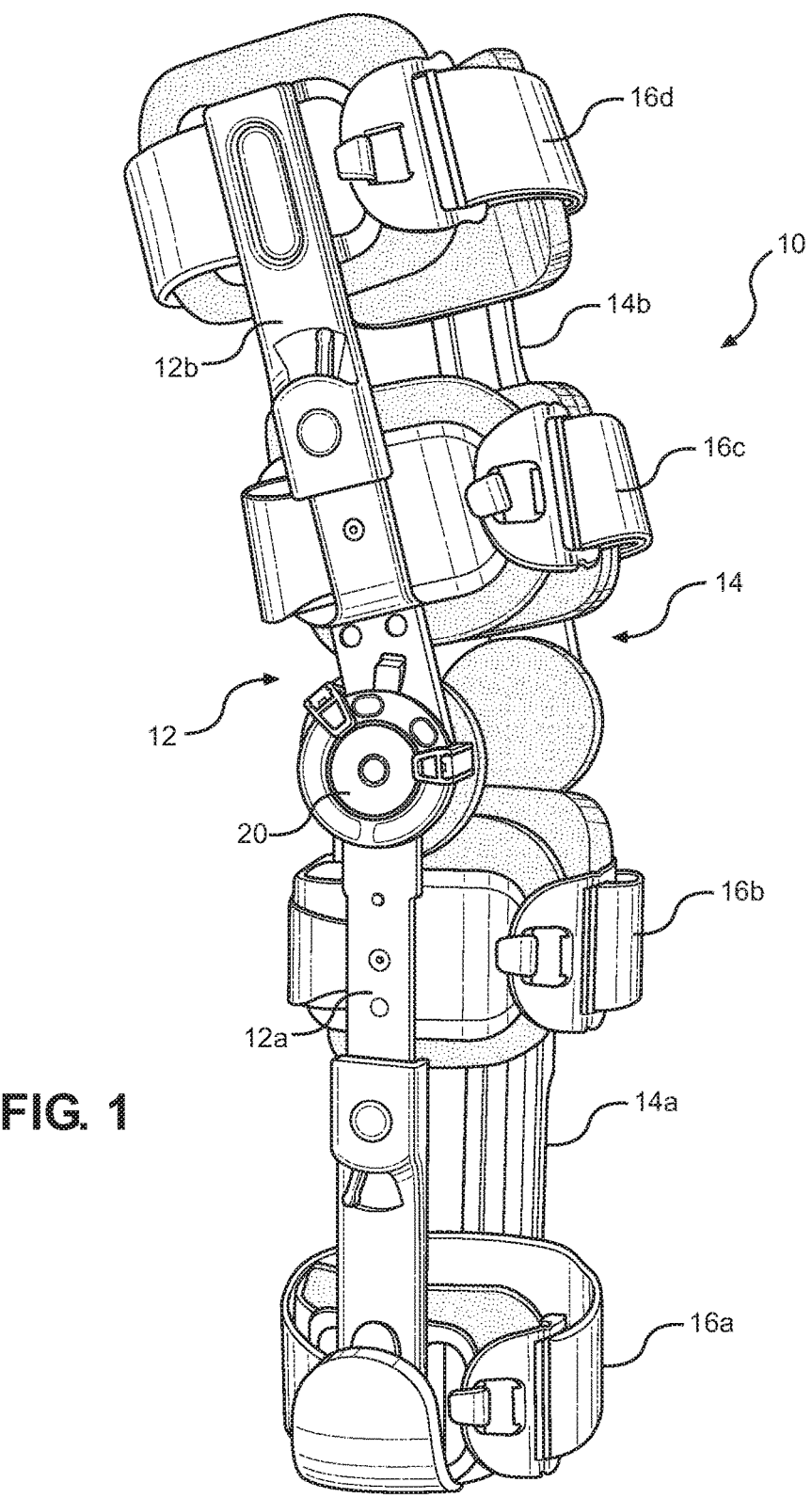
FIG. 1 is a perspective view showing a knee brace according to the disclosure.
Figure 2:
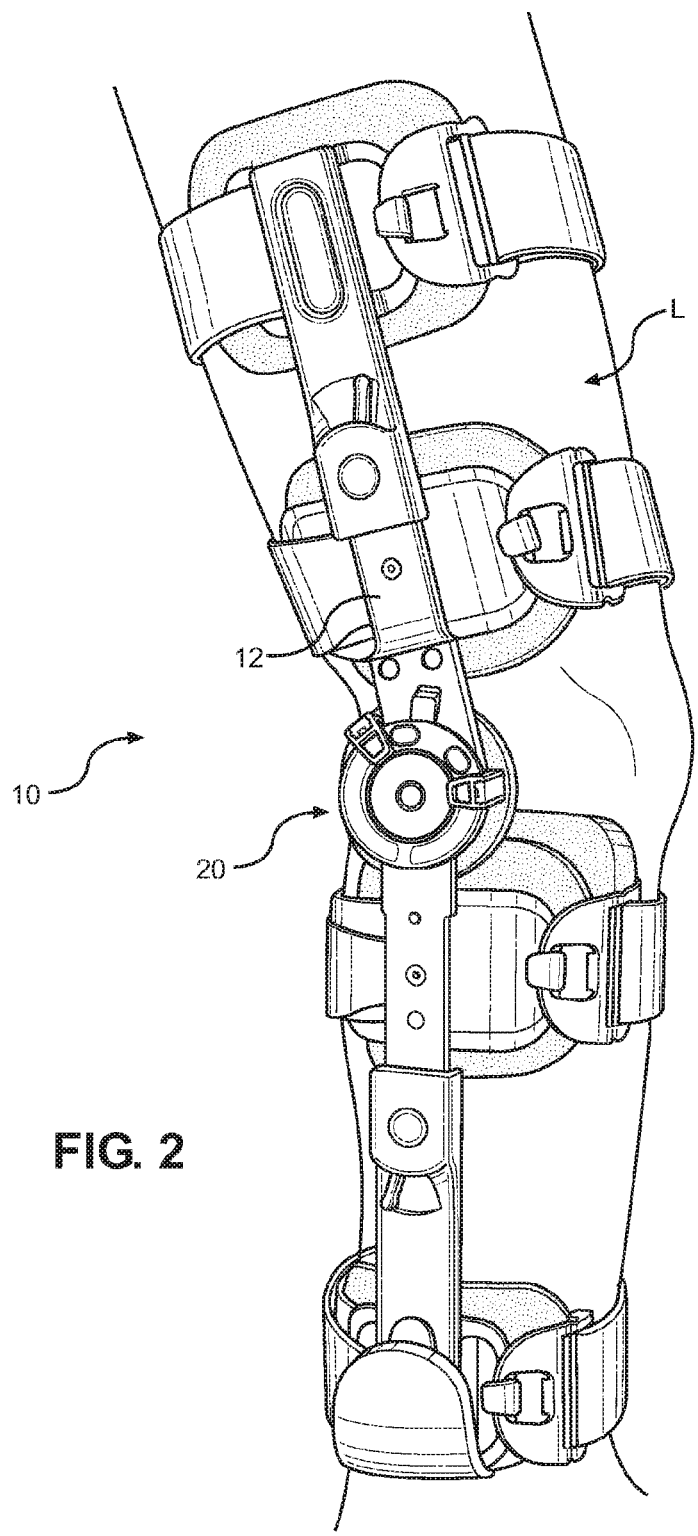
FIG. 2 shows the knee brace installed on a leg of a patient.
Figure 3:
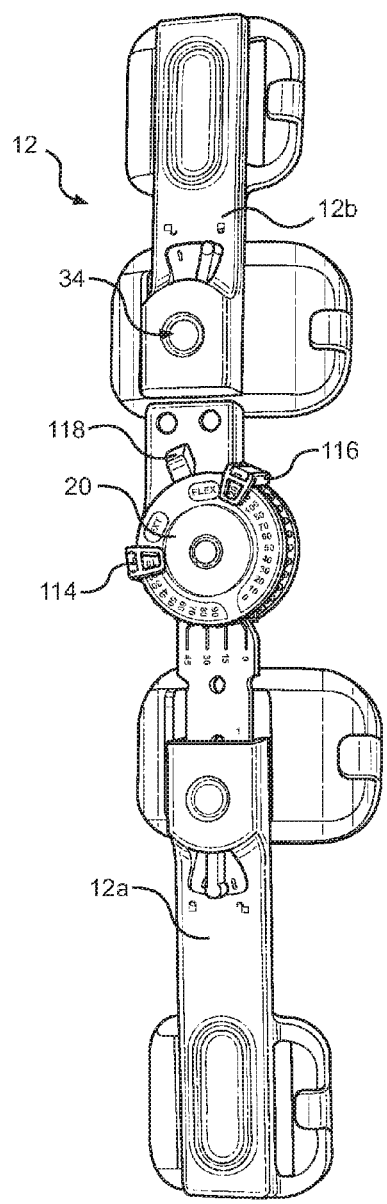
FIGS. 3 and 4 are assembled perspective views of a side of the knee brace of FIGS. 1 and 2.
Figure 4:
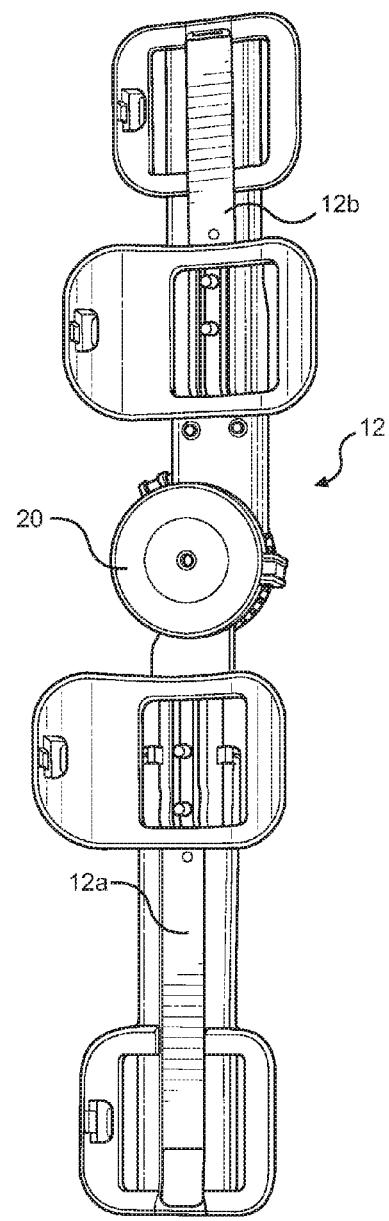

With reference to the drawings, the disclosure relates to an adjustable knee brace 10. The brace 10 includes a lateral telescoping strut assembly 12 and a medial telescoping strut assembly 14. In use, the lateral strut assembly 12 is located on the lateral side of a leg L, and the medial strut assembly 14 is located on a medial side of the leg L. Strapping, such as straps 16a, 16b, 16c, and 16d, extend between the strut assemblies 12 and 14 and around the leg L to hold the brace 10 in position on the leg L. The brace 10 may be constructed with only the strut assembly 12 or the strut assembly 14.

The lateral strut telescoping assembly 12 includes a lower leg strut 12a, an upper leg strut 12b, and a range of motion (ROM) hinge 20 hingedly connecting the lower leg strut 12a and the upper leg strut 12b. Similarly, the medial telescoping strut assembly 14 includes a lower leg strut 14a, an upper leg strut 14b, and a range of motion (ROM) hinge 22 hingedly connecting the lower leg strut 14a and the upper leg strut 14b.

The telescoping strut assemblies 12 and 14 of the brace 10 enable the brace 10 to fit a variety of patient sizes. Preferably, the brace 10 is adjustable to have a length of from about 18 inches to about 29 inches.

Figure 5:
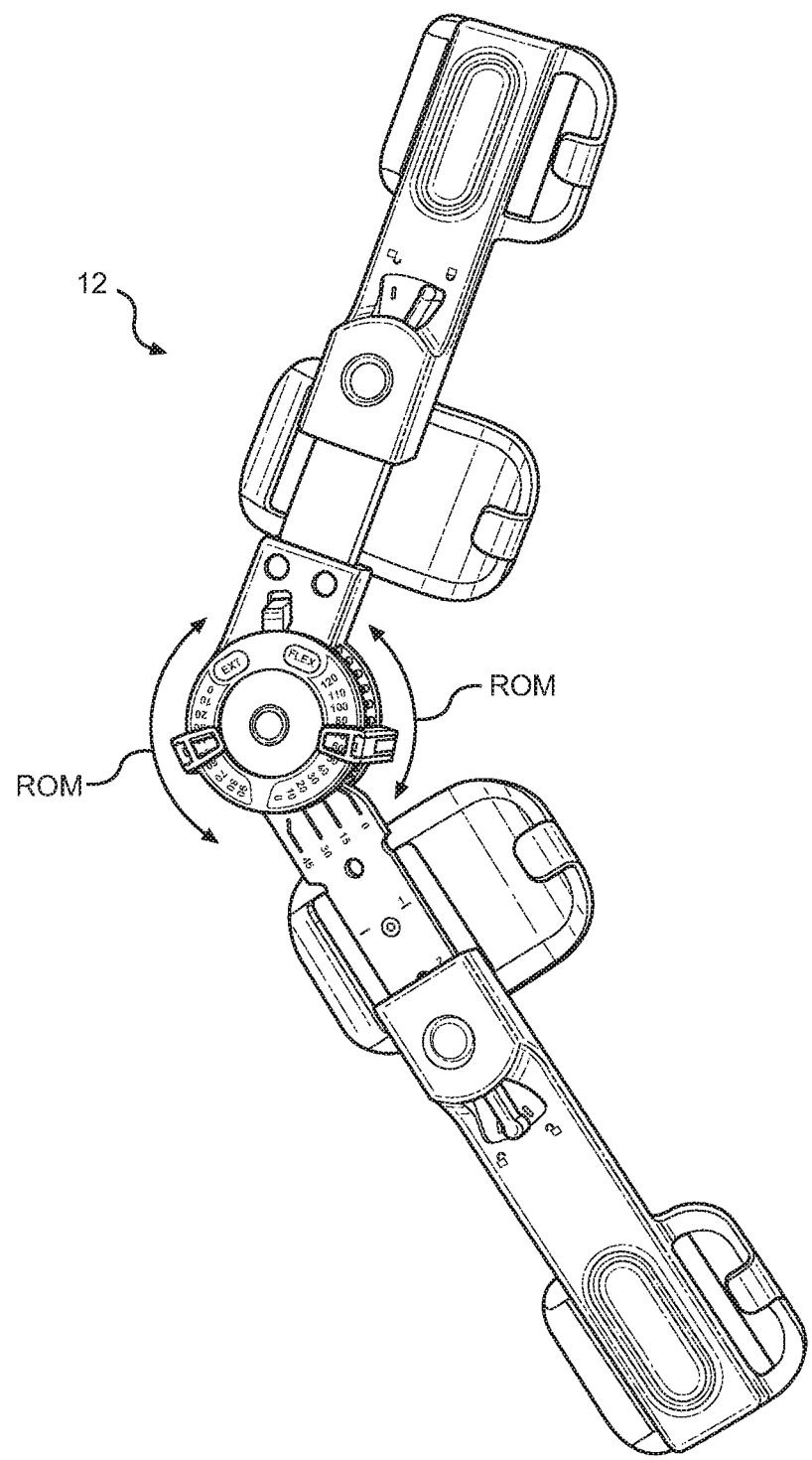
FIGS. 5 and 6 show the brace side of FIGS. 3 and 4 in different length and different flexion and extension positions.
Figure 6:
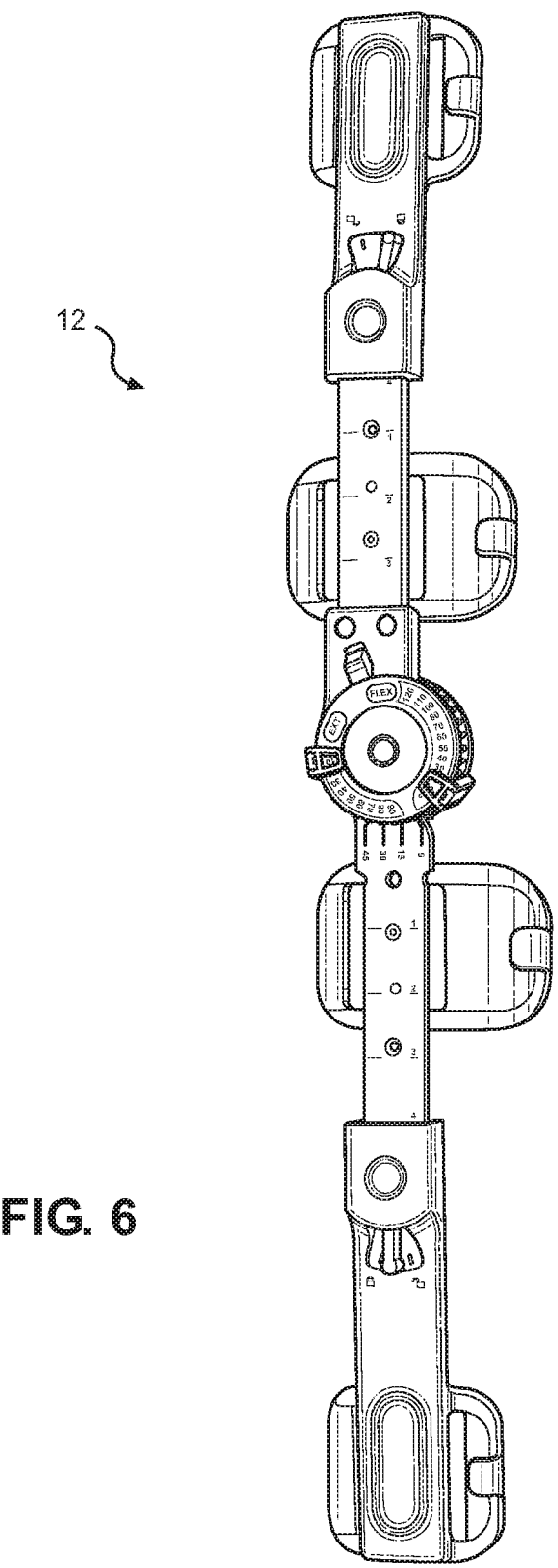
Figure 7:
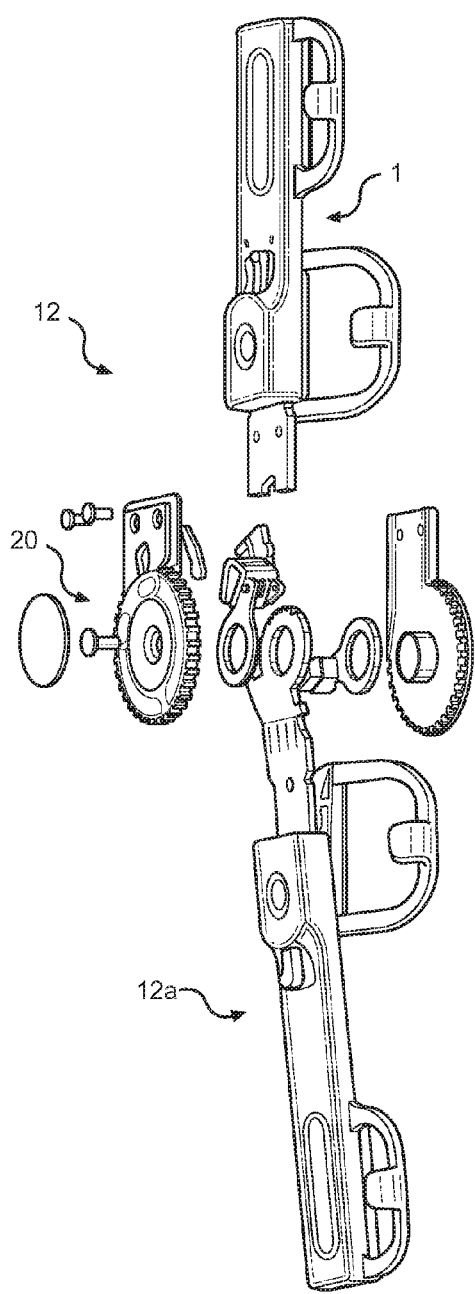
FIGS. 7 and 8 are partially exploded perspective views of the knee brace of FIGS. 3 and 4.
Figure 8:
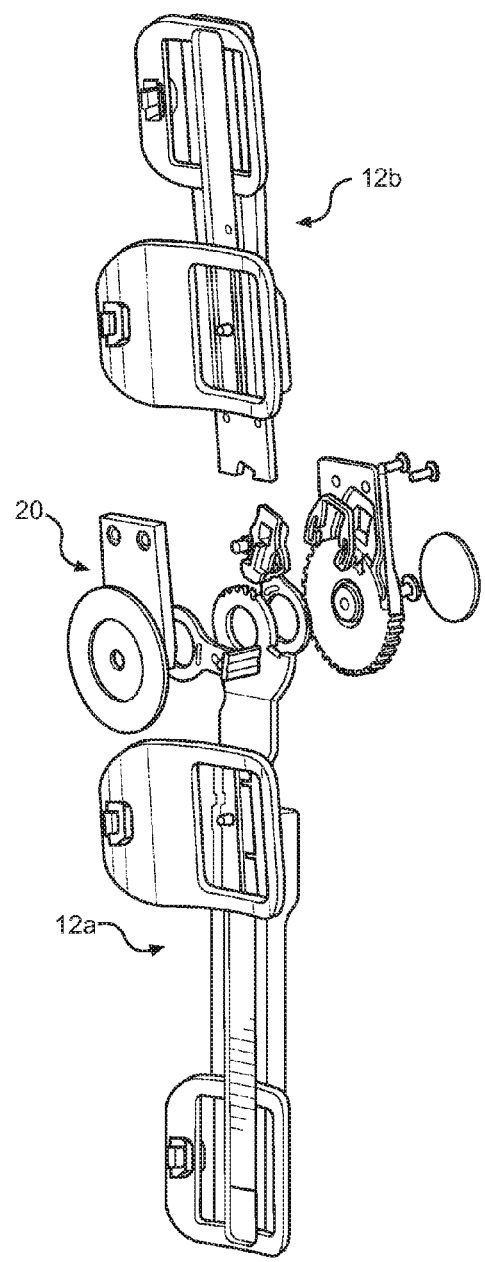
Figure 9:
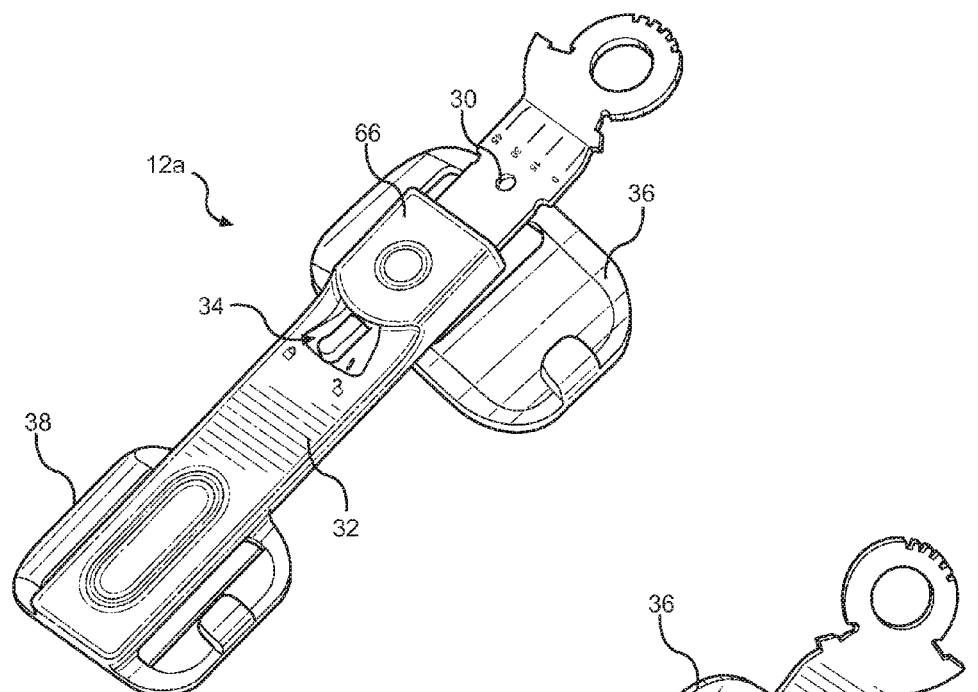
FIGS. 9 and 10 are assembled perspective views of a lower telescoping strut.
Figure 10:
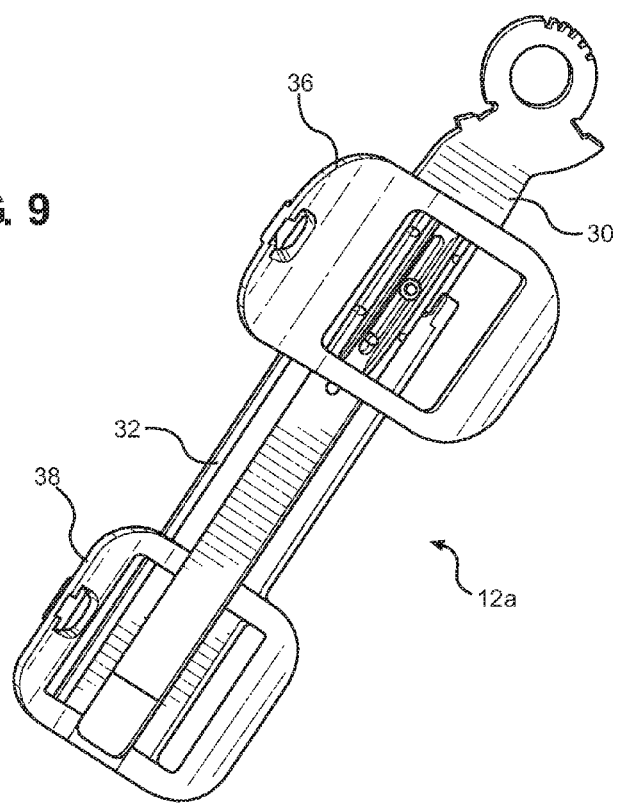
Figure 11:
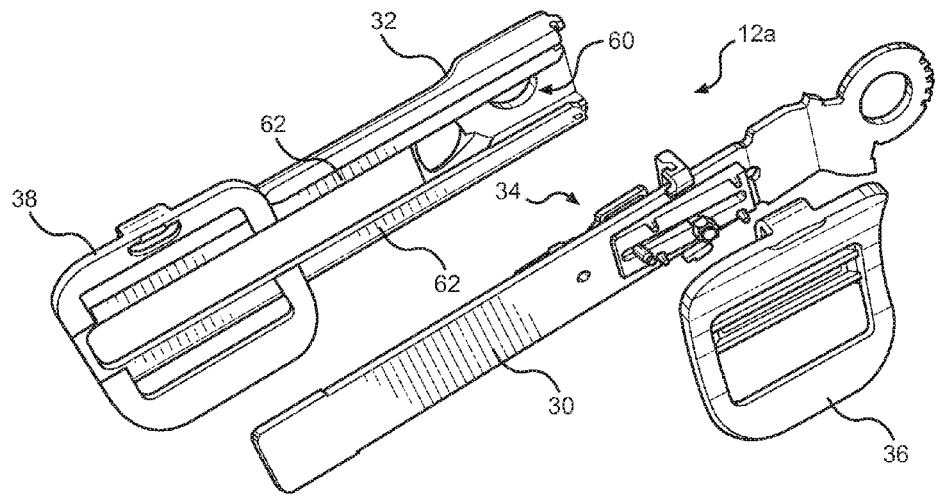
FIGS. 11 and 12 are partially exploded views of the lower telescoping strut of FIGS. 9 and 10.
Figure 12:
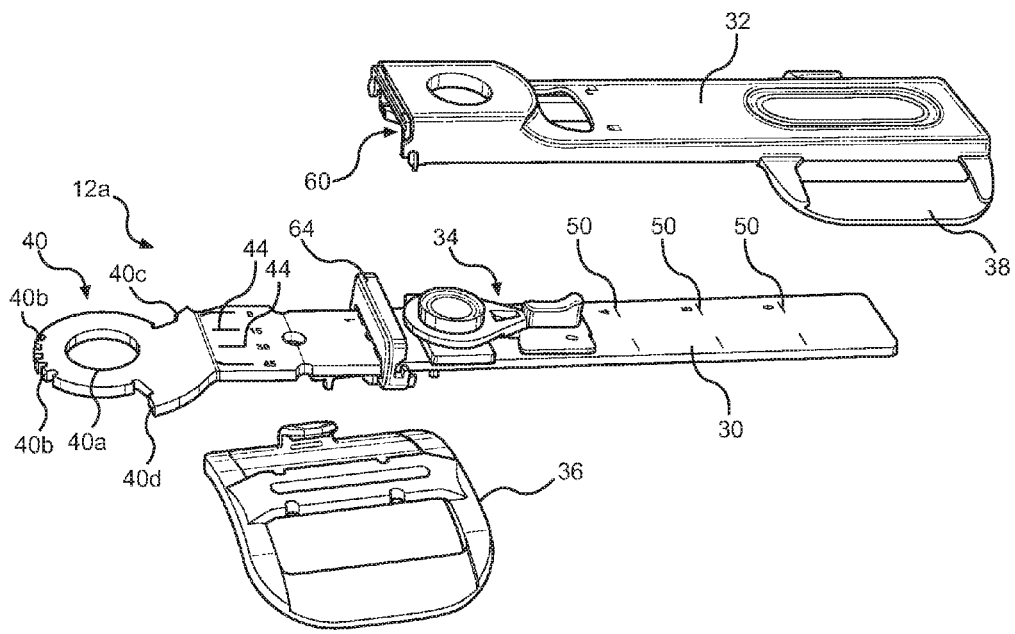
Figure 13:
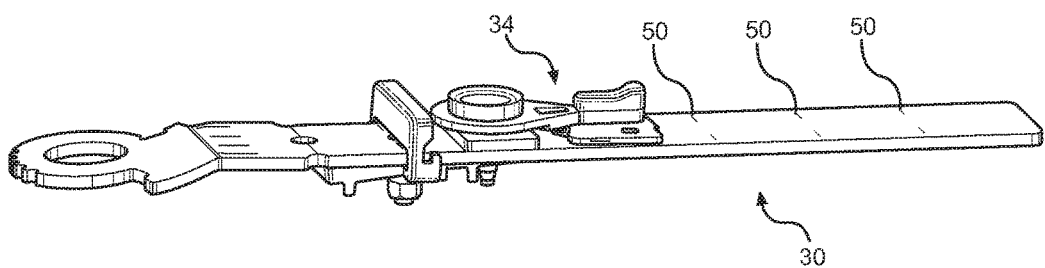
FIGS. 13 and 14 are partially assembled views of the lower telescoping strut of FIGS. 9 and 10.
Figure 14:
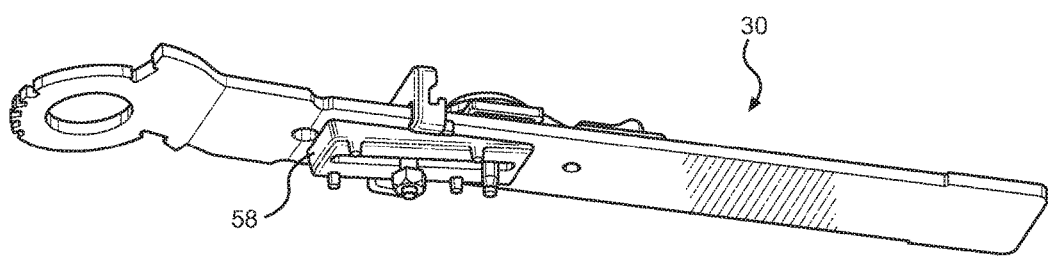
Figure 15:
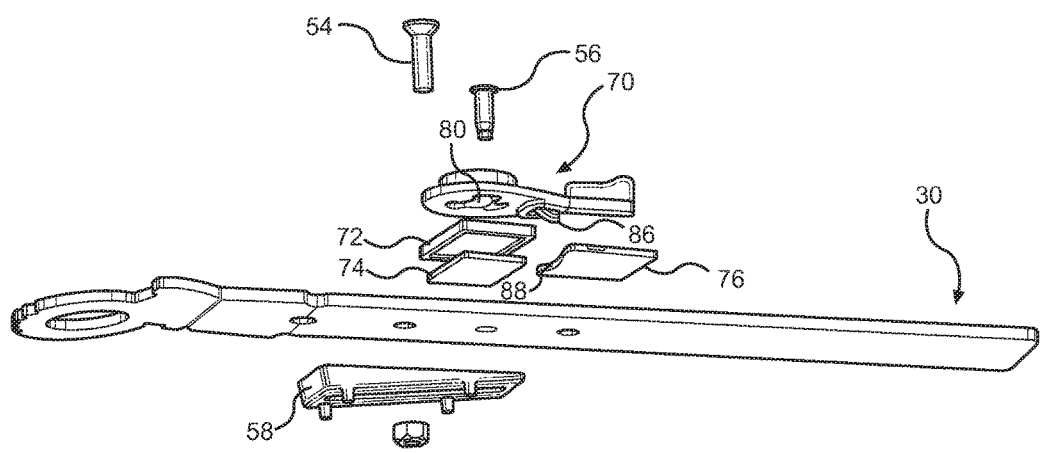
FIGS. 15 and 16 are exploded views of FIGS. 13 and 14.
Figure 16:
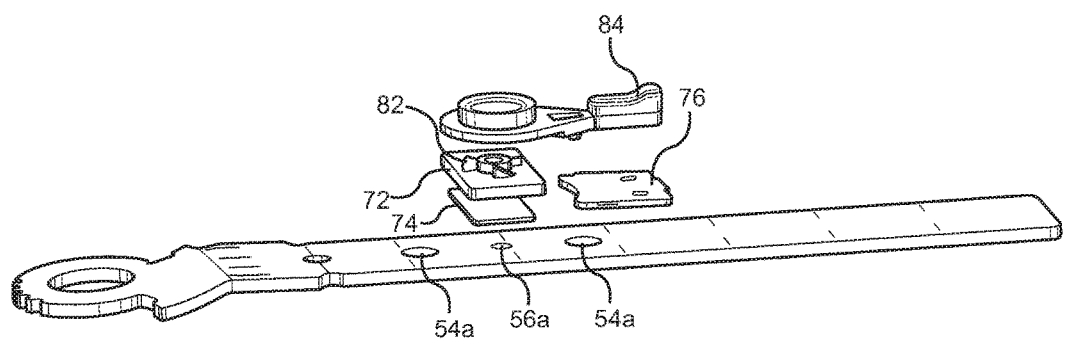
Figure 17:
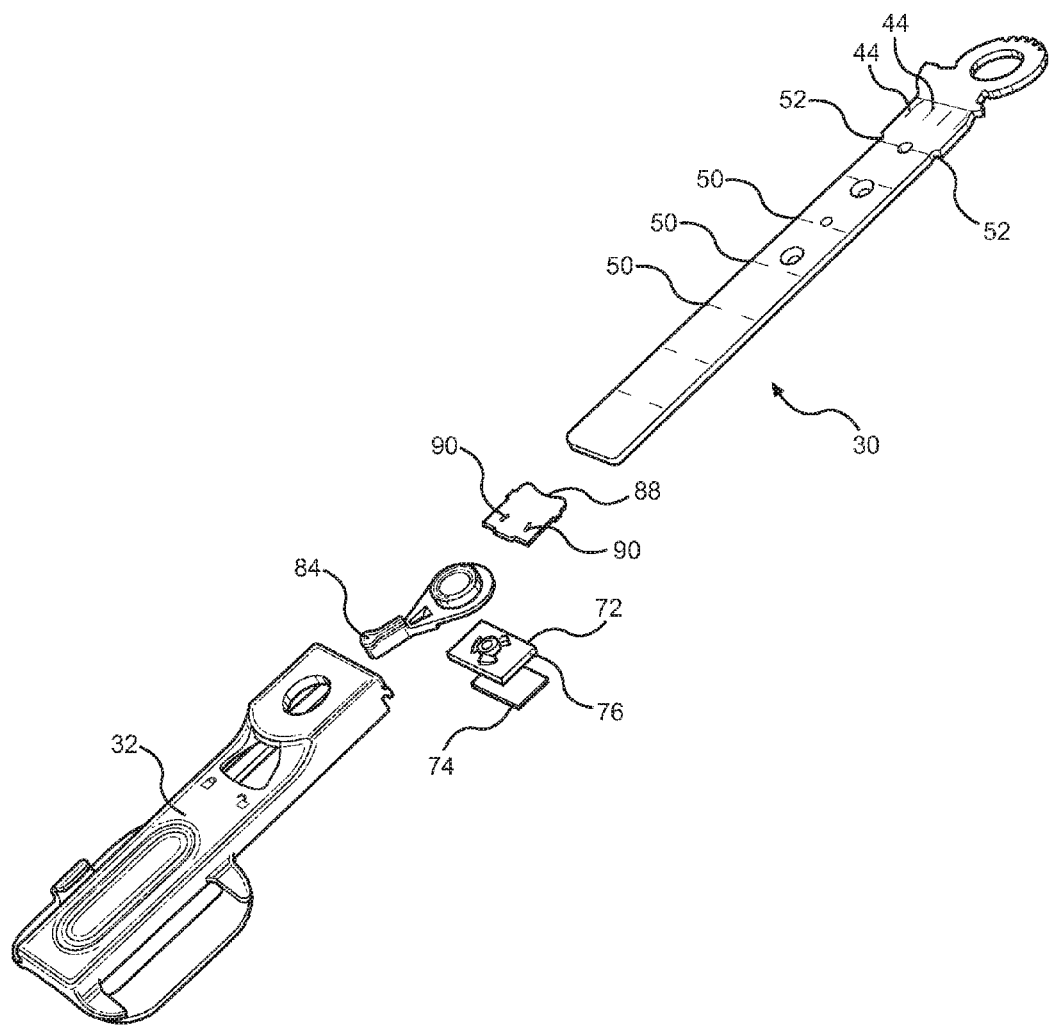
FIGS. 17 and 18 are partially exploded views of portions of the lower telescoping strut of FIGS. 9 and 10.
Figure 18:
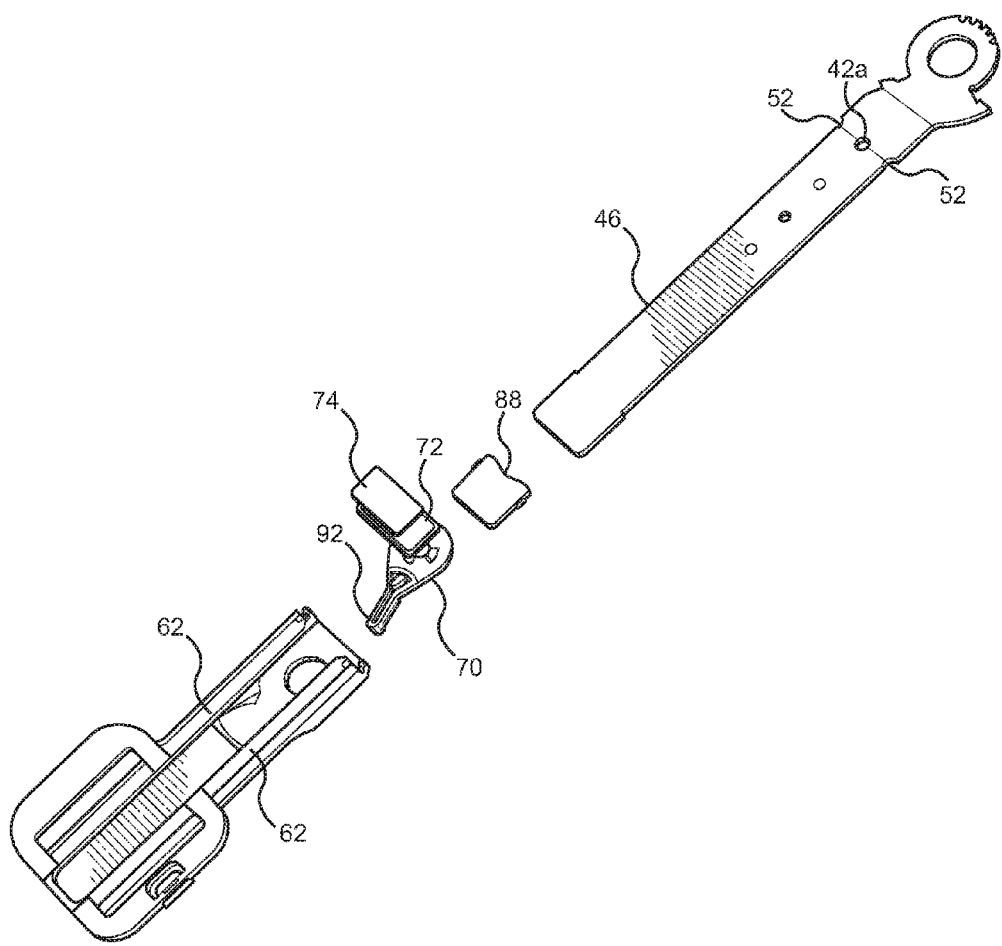

As represented in FIGS. 5 and 6, the range of motion hinges, such as the hinge 20, enable desired adjustment of flexion and extension settings of the brace to provide knee immobilization or range of motion limitations as prescribed by a medical practitioner. The hinge 20 permits radial or rotational movement of the leg struts 12a and 12b, as represented by the arrows ROM, in the plane of the leg struts 12a and 12b.

Knee flexion is characterized as a bending the knee joint resulting in a decrease of angle, and involving movement of the lower leg toward the back of the thigh. Knee extension is characterized as a straightening of the knee joint resulting in an increase of angle, and involving movement of the lower leg away from the back of the thigh.

The brace 10 is desirably suitable to be used post-injury, postoperatively or throughout rehabilitation. The brace 10 is generally adjusted to fit about two inches below the groin and about two inches above the ankle bones of the patient.

The lateral telescoping strut assembly 12 and the medial telescoping strut assembly 14 are substantially identical to one another. Accordingly, for the sake of brevity, only the lateral telescoping strut assembly 12 is described in detail herein, it being understood that the medial strut 14 is substantially identical thereto. Likewise, the ROM hinge 20 and the ROM hinge 22 are substantially identical to one another, and only the ROM hinge 20 is described in detail herein.

With additional reference to FIGS. 9-18, the lower leg strut 12a is configured to cooperate with the ROM hinge 20 and to telescopically adjust in length. The lower strut 12a includes a strut member 30, a receiver 32, and a latch assembly 34. A pair of pad mounts 36 and 38 attach to the strut 12a for locating pads for contacting the leg of the user and for receiving the straps 16a and 16b. The receiver 32 is telescopically positionable relative to the strut member 30. The latch assembly 34 is housed on the receiver 32 and may be placed in an unlatched orientation to permit the strut member 30 to telescope relative to the receiver 32, and the latch assembly 34 may be placed in a latched orientation to frictionally couple the strut member 30 to the receiver 32 to inhibit relative movement.

The strut member 30 may be an elongate, thin, flat bar preferably made of a rigid metal material, having an overall length of about ten inches. The strut member 30 is generally rectangular, but configured to have an upper end 40 configured to receive and cooperate with the ROM hinge 20. In this regard, the upper end 40 is generally circular with a central aperture 40a. An uppermost crown portion of the upper end 40 includes teeth 40b, and lower shoulder portions of the upper end 40 define a flexion range of motion stop 40c and an extension range of motion stop 40d. The upper end 40 represents about two inches of the overall length of the strut member 30.

Below the upper end is a bend zone 42, representing about one inch of the overall length. The bend zone 42 is configured to be bent to enable the strut member 30 to conform to patient anatomy. The bend zone 42 may include a central aperture 42a in the strut member 30 to promote a uniform bend. To bend the bend zone 32, the bend zone 42 may be placed against the edge of a hard surface (table, desk, etc.) and a gradual force is applied to the strut member 30 while holding the ROM hinge 20 and the upper leg strut 12b steady until the desired amount of bend is achieved. Drop lock preset indicia 44, such as 0, 15, 30, 45 degree markings, are located on the outer surface of the bend zone 42 to cooperate with the ROM hinge 20 to indicate pre-set lock settings of the extension angle of the brace. A lower end 46 of the strut member 30 is generally rectangular and represents about seven inches of the overall length of the strut member 30.

Indicia or indicium, such as one inch increment indicia 50 is located on the outer facing surface of the strut member 30 for facilitating adjustment of the length of the strut 12a by adjusting the receiver 32 relative to the strut member 30. The width dimension of the lower end 46 is less than that of the bend zone 42 to define abutments 52 that limit travel of the receiver 32 relative to the strut member 30 and defines the shortest length of the strut 12a.

The pad mount 36 is connected to the strut member 30 as by a fastener 54 and a mounting stud 56 that extend through apertures 54a and 56a, respectively, of the strut mount 30 and a wedge shaped spacer 58, as best seen in FIGS. 11-16. An extra aperture 54a is also shown to permit further adjustment of the location of the pad mount 36 if desired. The wedge shaped spacer 58 advantageously enables the pad mount 36 to be a separate piece and locates the pad mount 36 to better conform to the leg of the patient. In this regard, the wedge shaped spacer 58 may be provided having different slopes and thicknesses to enable a more custom fit to the leg of the patient.

The receiver 32 may be of one piece molded plastic construction and provides an elongate housing having an interior channel 60 defined by a pair of spaced apart rails 62. The channel 60 is sized and configured for slidingly receiving the strut member 30. A plastic cover 64 may be provided to overlie the juncture of the channel 60 and the strut member 30 when the receiver 32 is installed on the strut member 30. A latch housing 66 is defined on the receiver 32 for housing and locating the latch assembly 34 on the receiver 32. The pad mount 38 may be formed integrally with the receiver 32 during molding of the receiver 32.

The latch assembly 34 is located within the latch housing 66 of the receiver 32. The latch assembly 34 includes a movable and preferably pivotable member 70, a cam base 72 having a friction member 74 located on a lower surface thereof, and a latch plate 76. In basic operation of the latch assembly 34, the member 70 is moved, preferably by pivoting about one quarter revolution to selectively bear or release the friction member 74 from pressured engagement with the strut member 30. Thus, when the friction member 74 is pressured against the strut member 30, the strut member 30 is locked from sliding relative to the receiver 32. When pressure bearing the friction member 74 against the strut member 30 is released by pivoting the pivotable member 70 in the opposite direction, the strut member 30 may be telescoped relative to the receiver to enable incremental adjustment of the length of the strut member 12a. The pivotable member 70 is then returned to the locked position to maintain the strut member 12a at the desired adjusted length.

The pivotable member 70 and the cam base 72 may each be of one piece molded plastic construction. The pivotable member 70 is pivotally located within the housing 66 to sit atop the cam base 72, with the friction member 74 facing the strut member 30 located in the receiver 30. The vertical position of the pivotable member 70 is fixed within the housing 66. The pivotable member 70 has a lower surface with a cam cavity 80 defined thereon configured to seat onto and pivotally cooperate with a cam surface 82 of the cam base 72. The pivotable member 70 may include a lever 84 that a user a user grasps to pivot the pivotable member 70.

The cam surface 82 may be provided by an alternating series of ramped and flat surfaces and the cam cavity 80 provided as a negative contour of the cam surface 82. In one pivotal orientation of the pivotable member 70, the cam cavity 80 is aligned with and nests with the cam surface 82. In another pivotal orientation of the pivotable member 70, the cam surface 82 and the cam cavity do not nest and the corresponding surfaces are out of phase to bear the cam base 72 away from the pivotable member 70.

Accordingly, when the pivotable member 70 is pivoted in one direction, such as one quarter turn clockwise, the cam cavity 80 and the cam surface 82 cooperate to bear the cam base 72 away from the pivotable member 70 so as to pressure the friction member 74 against an adjacent surface of the strut member 30 received by the rails 62 of the receiver 32. This orientation is understood to provide a locked position of the latch assembly 34. When the pivotable member 70 is returned to its starting or unlocked position, such as pivoting one quarter turn in the opposite direction, the cam surface 82 can align and seat within the cam cavity 80 and release the pressure bearing the friction member 74 against the strut member 30.

Figure 19A:
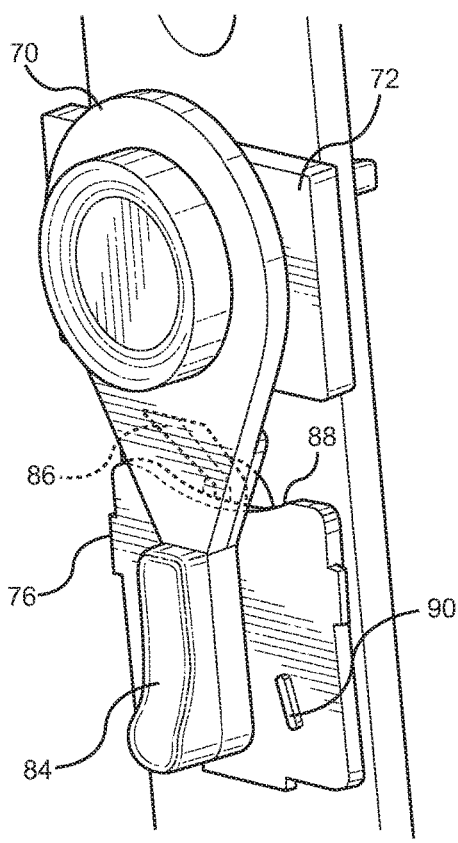
FIGS. 19A and 19B are close up views of a latch assembly of the lower telescoping strut of FIGS. 9 and 10.
Figure 19B:
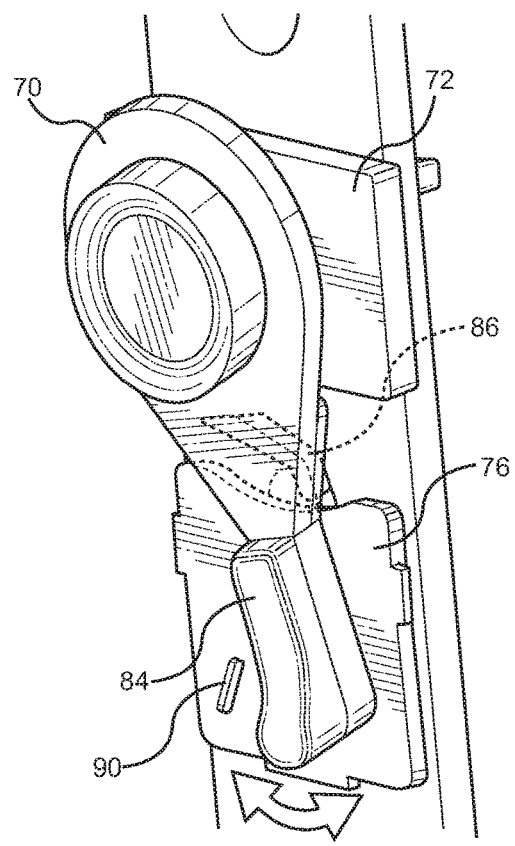
Figure 20:
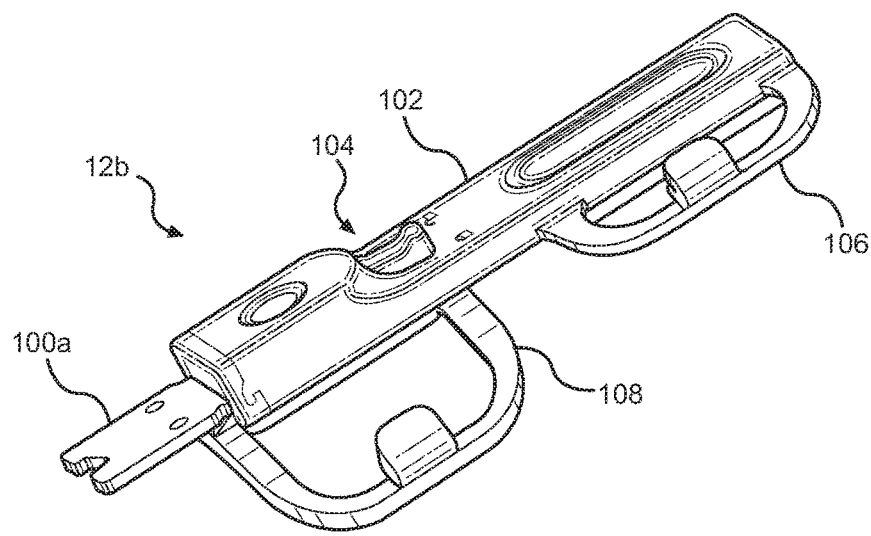
FIGS. 20 and 21 show an upper telescoping strut.

The latch plate 76 is configured to engage the pivotable member 70 to selectively maintain it in the locked or the unlocked position. The latch plate 76 is a flat plate, preferably plastic, secured within the housing 66 so as to underlie the lever 84 of the pivotable member 70. A tongue 86 extends from a lower surface of the lever 84 to follow and bear against a curved edge 88 of the latch plate 76 to provide a frictional resistance against free movement of the pivotable member 70. In addition, an upper surface of the latch plate 76 includes raised bumps 90 at locations corresponding to the position of the lever 84 when the pivotable member 70 is locked and unlocked. A groove 92 located on the underside of the lever 84 receives one of the bumps 90 when the pivotable member 70 is in the locked position of the unlocked position to further serve to maintain the latch assembly 34 in a locked or unlocked state (FIGS. 19A and 19B).

Figure 21:
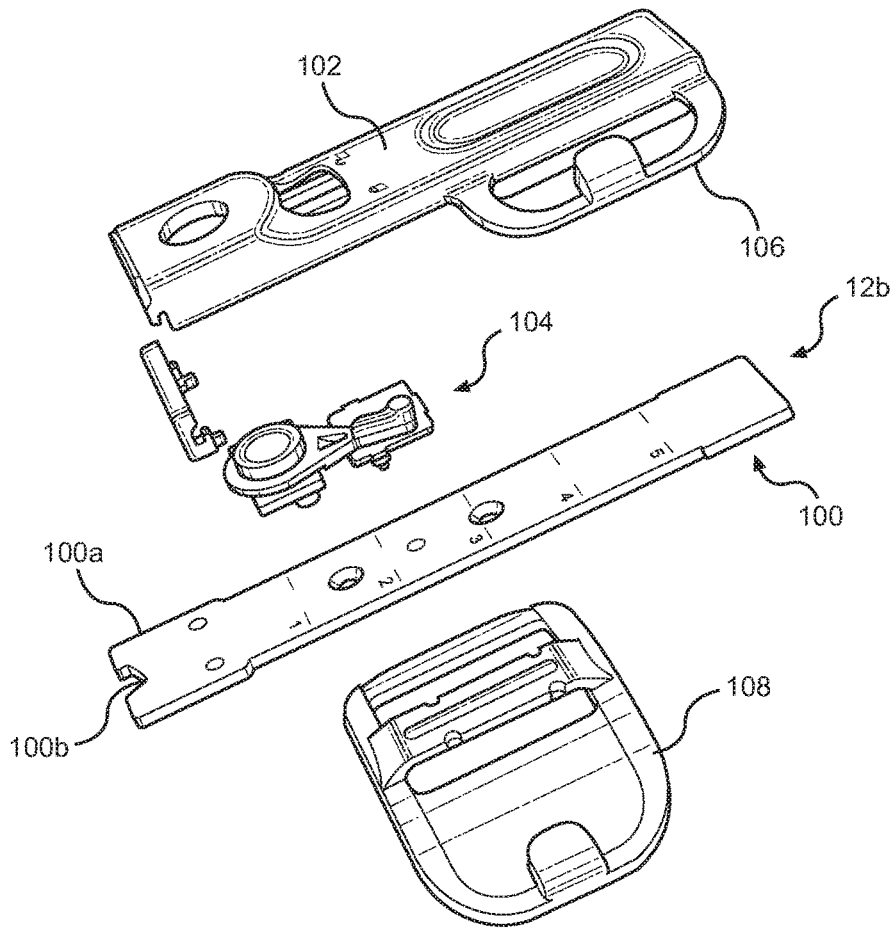
Figures 22, 23:
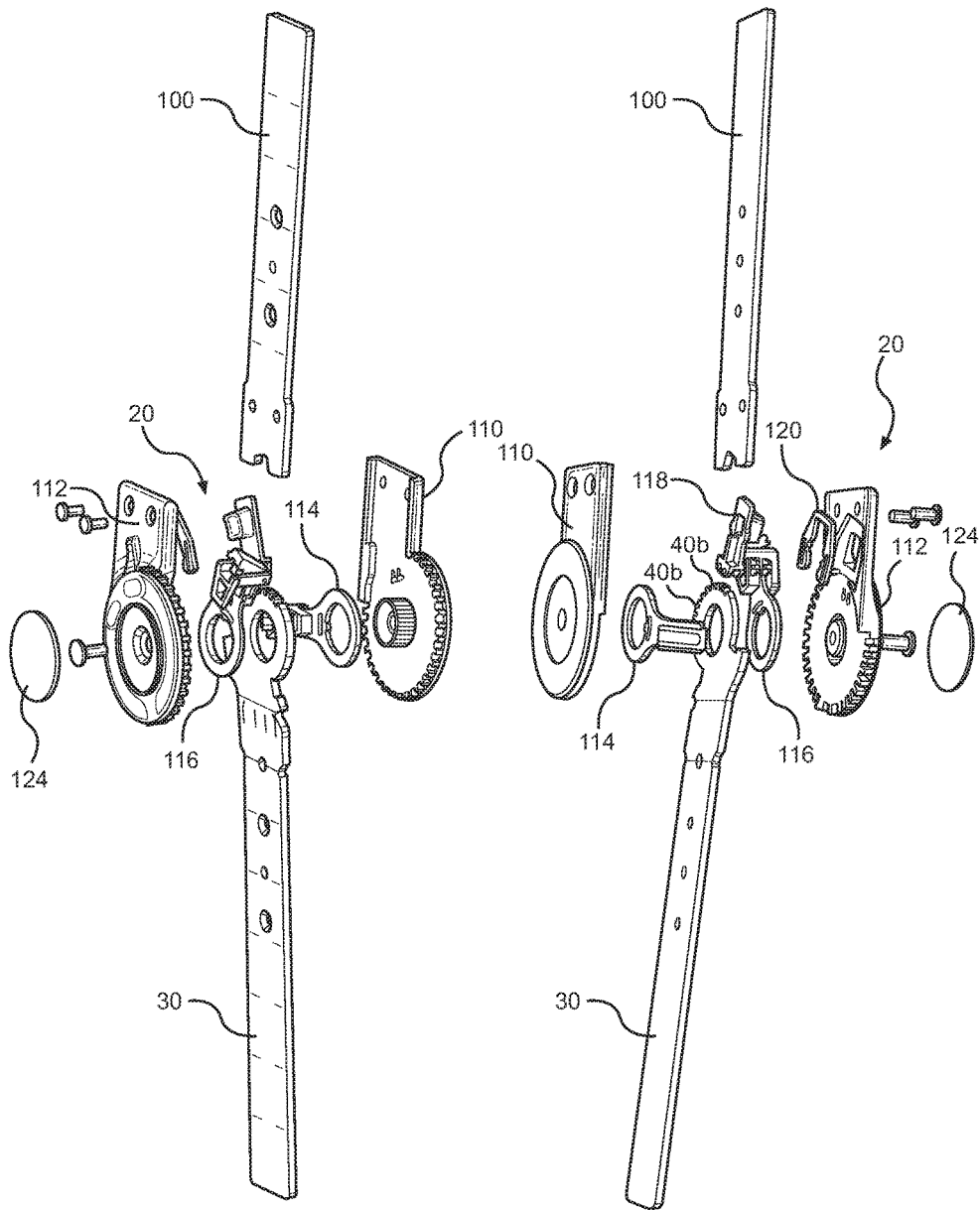
FIGS. 22 and 23 are exploded views showing a range of motion hinge.
Figure 24:
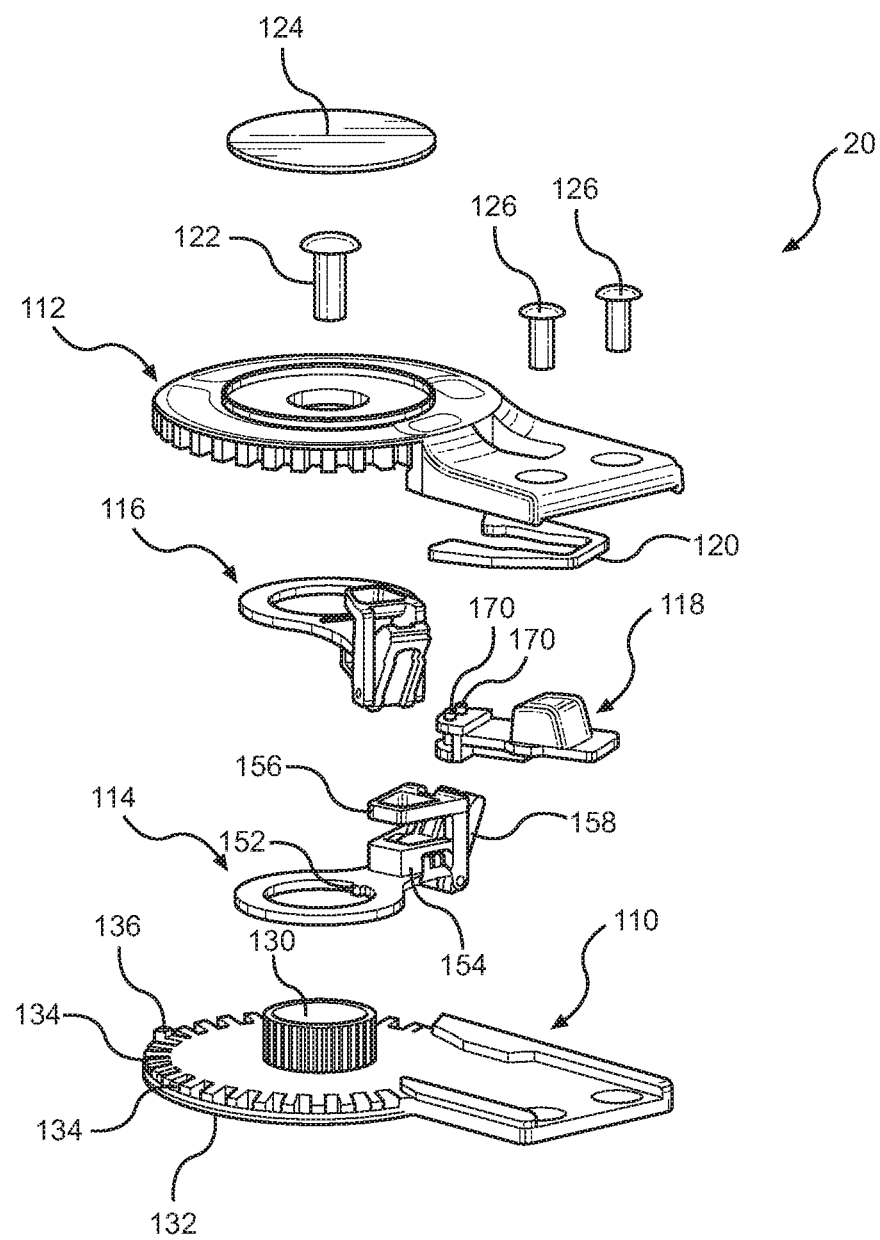
FIGS. 24 and 25 are close-up exploded views of the range of motion hinge.
Figure 25:
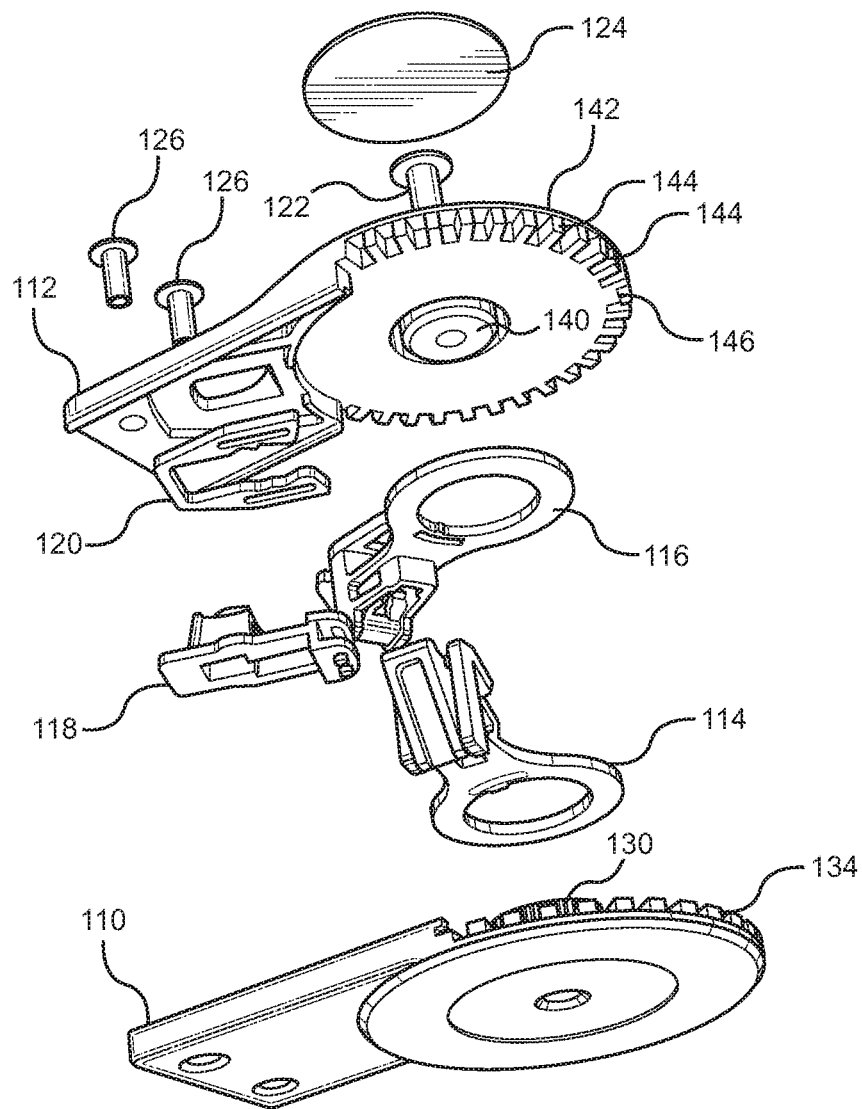
Figure 26:
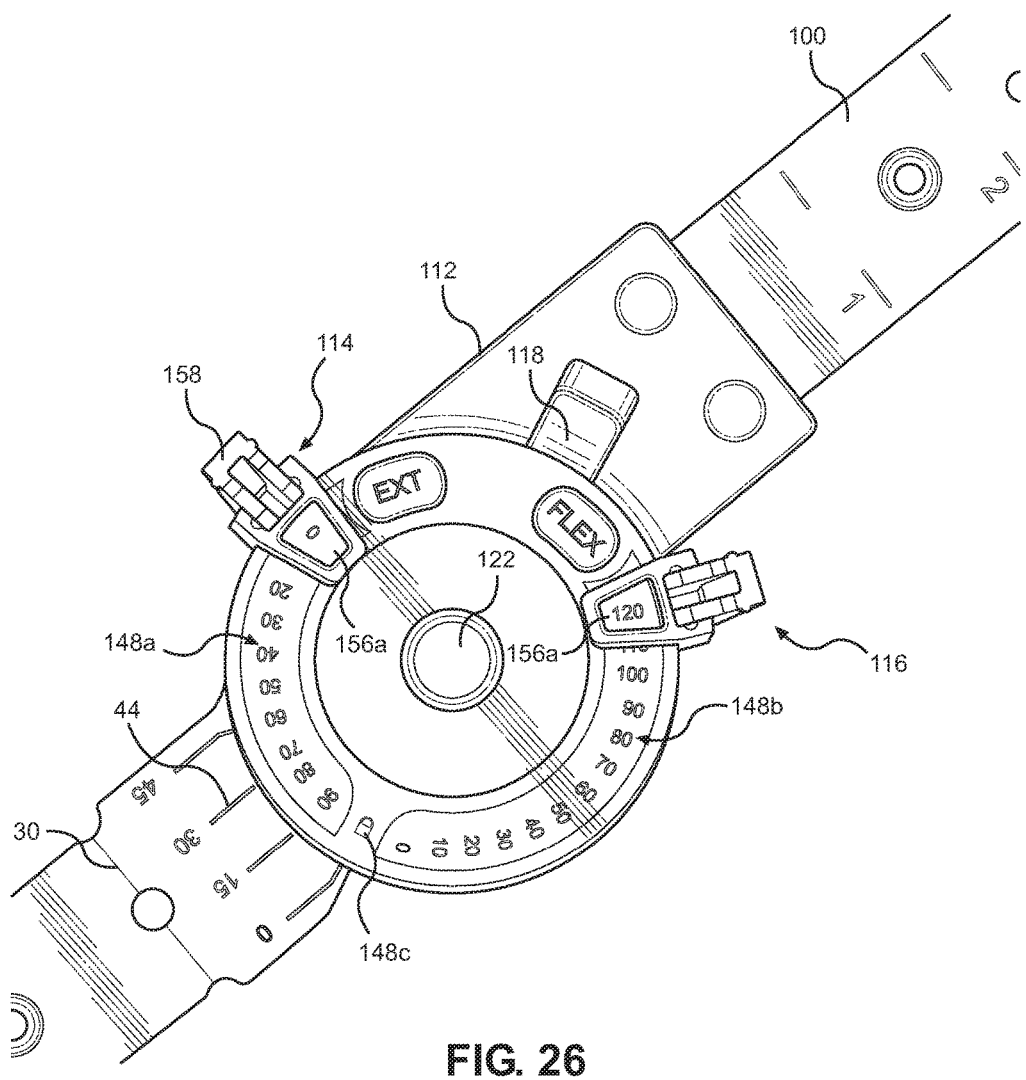
FIGS. 26-29 show assembly of the range of motion hinge.
Figure 27:
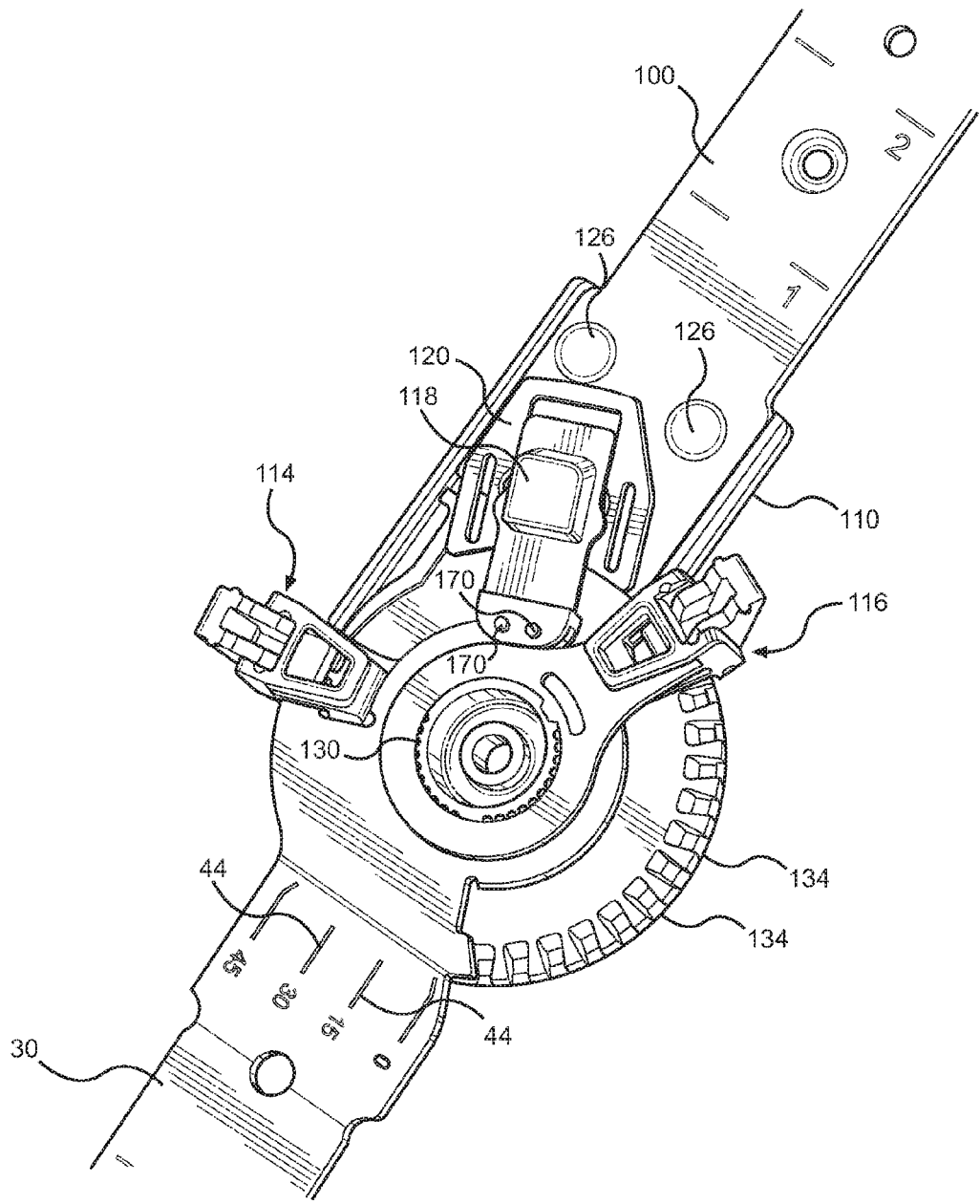
Figure 28:
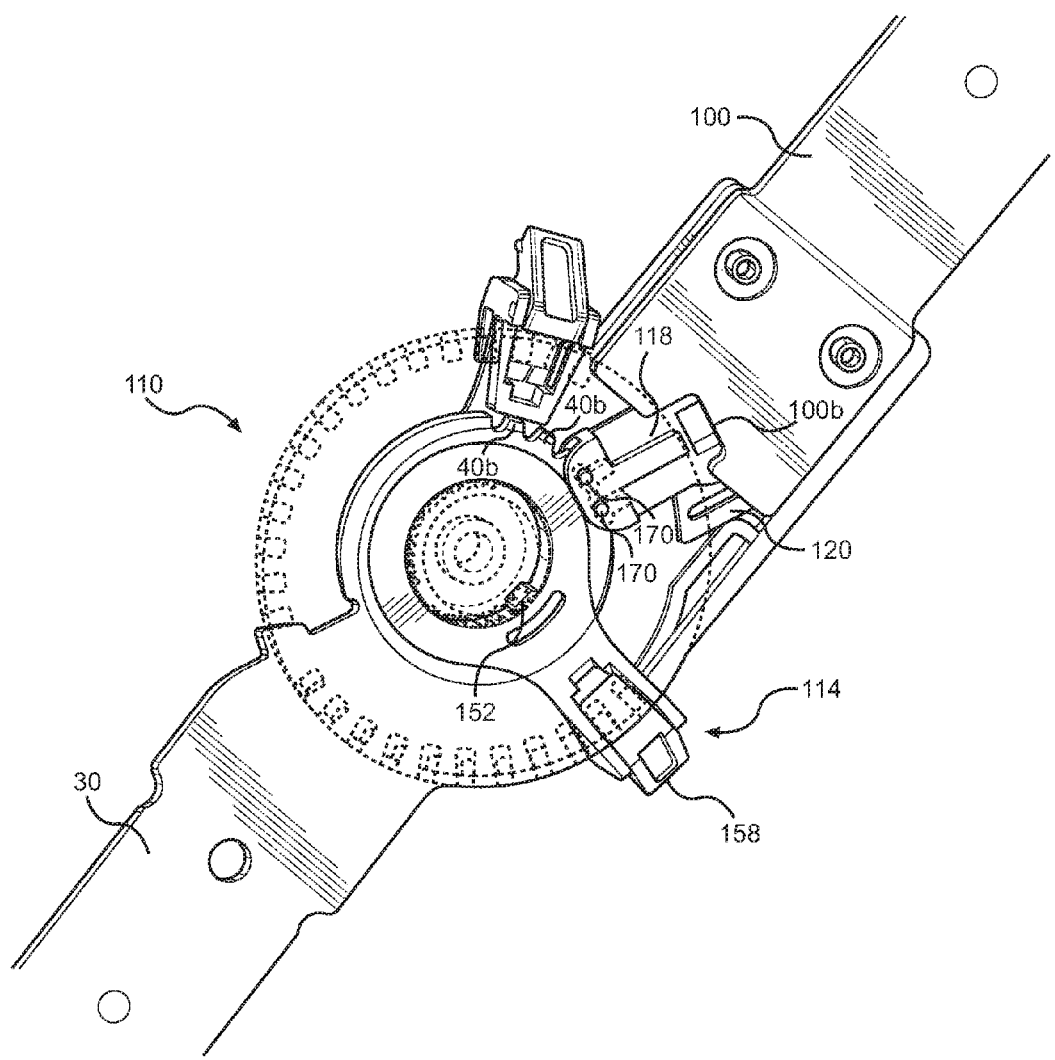

With reference to FIGS. 21 and 22, the upper leg strut 12b is similar to the lower leg strut 12a and is configured to cooperate with the ROM hinge 20 and to telescopically adjust in length. The upper strut 12b includes a strut member 100, a receiver 102, and a latch assembly 104. A pair of pad mounts 106 and 108 attach to the strut 12b for locating pads for contacting the leg of the user and for receiving the straps 16c and 16d. The receiver 102 is telescopically positionable relative to the strut member 100. The latch assembly 104 is housed on the receiver 102 and may be placed in an unlatched orientation to permit the strut member 100 to telescope relative to the receiver 102, and the latch assembly 104 may be placed in a latched orientation to frictionally couple the strut member 100 to the receiver 102 to inhibit relative movement.

The strut member 100 is similar to the strut member 30, except it does not include a circular end or a bend zone. The strut member 100 includes a lower end 100a configured to receive and cooperate with a different portion of the ROM hinge 20 than the member 30. In this regard, the lower end 100a is square, and includes an inset notch 100b. The receiver 102 is substantially identical to the receiver 32, and the latch assembly 104 is substantially identical to the latch assembly 34.

With additional reference to FIGS. 22-30, the range of motion hinge 20 is configured to enable desired adjustment of flexion and extension settings of the brace to provide knee immobilization or range of motion limitations as prescribed by a medical practitioner. The hinge 20 includes a hinge plate 110, a hinge plate 112, an extension stop 114, and a flexion stop 116. The hinge plate 110 and the extension stop 114 are located on one side of the upper end 40 of the strut member 30. The hinge plate 112 and the extension stop 116 are located on the opposite side of the upper end 40 of the strut member 30. The hinge 20 also includes a lock lever 118 slidingly mounted by a mount 120 to enable knee immobilization at a desired orientation. A central fastener such as a rivet 122 extends between the hinge plates 110 and 112 to hold the hinge 20 together. A rivet cover 124 may be provided for aesthetics. Fasteners, such as rivets 126 attach the hinge plates 110 and 112 to the strut member 100.

The hinge plate 110 is configured with an interior central splined shaft 130 configured to extend through the central aperture 40a of the strut member 30. A semi-circular peripheral edge 132 of the hinge plate 110 is provided to accommodate the range of extension offered by the hinge 20 (preferably about 90 degrees) and the range of flexion offered by the hinge 20 (preferably about 120 degrees). Thus, the edge 132 is greater than about 210 degrees, and preferably about 240 degrees. The interior periphery of the edge 132 includes incremental and uniformly spaced apart cuts or keys 134 configured for cooperating with the stops 114 and 116. The keys 134 are coordinated with the splines of the shaft 130. A stop 136 is located between the portion of the edge 132 provided for extension adjustment and the portion provided for flexion adjustment.

The hinge plate 112 is configured to mate with the hinge plate 110. The hinge plate 112 is a mirror image of the hinge plate 110, except instead of having the splined shaft 130, the interior of the plate 112 includes a central receiver 140 that rotationally receives the smooth distal end of the shaft 130. The hinge plate 112 includes a semi-circular peripheral edge 142 corresponding to the edge 132 of the hinge plate 110. The hinge plate 112 similarly includes keys 144 corresponding to the keys 143, and a stop 146 corresponding to the stop 136. The exterior surface of the hinge plate 112 includes extension indicia 148a corresponding to the extension angle of the brace, flexion indicia 148b corresponding to the flexion angle of the brace, and lock indicia 148c that aligns with the drop lock indicia 44 to indicate preset knee extension angles to which the brace may be locked by use of the lock lever 118.

The extension stop 114 and the flexion stop 116 are substantially identical to one another. The extension stop 114 sets a limit on extension movement of the knee, and the flexion stop 116 sets a limit on flexion movement of the knee. Only the extension stop 114 is described in detail herein, it being understood that the flexion stop 116 is substantially identical thereto.

The extension stop 114 is of molded plastic construction and includes a ring 150 configured to fit onto the splined shaft 130. A detent 152 on the interior of the ring 150 cooperates with the splines of the shaft 130 to enable incremental rotational adjustment of the stop 114 about the shaft 130. A spacer 154 spans the gap between the hinge plates 110 and 112 at the periphery of the plates 110 and 112 of the assembled hinge 20. A position indicator 156 of the stop 114 extends to be located to provide an indicator window 156a that overlies a portion of the hinge plate 112 to indicate the degree of extension the hinge 20 is adjusted to.

Figure 29:
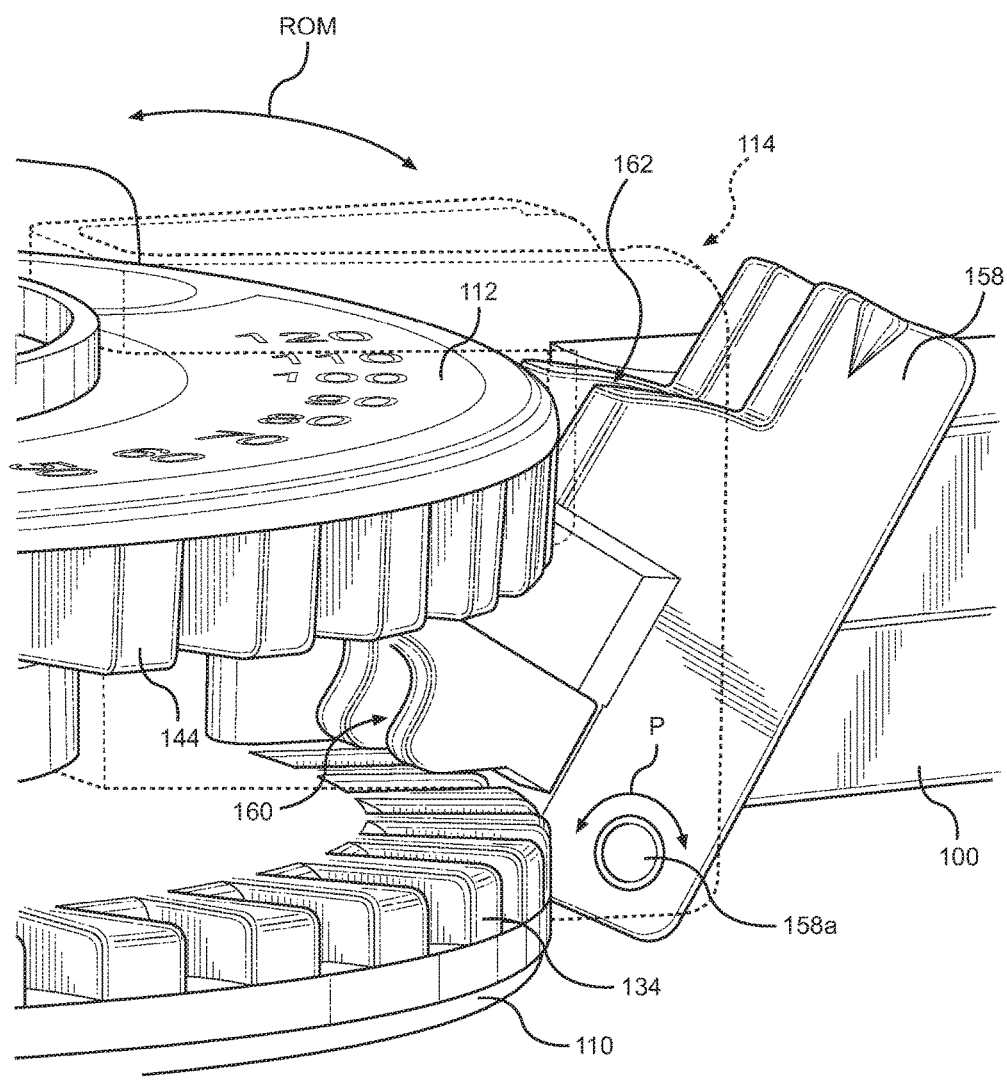
Figure 30:
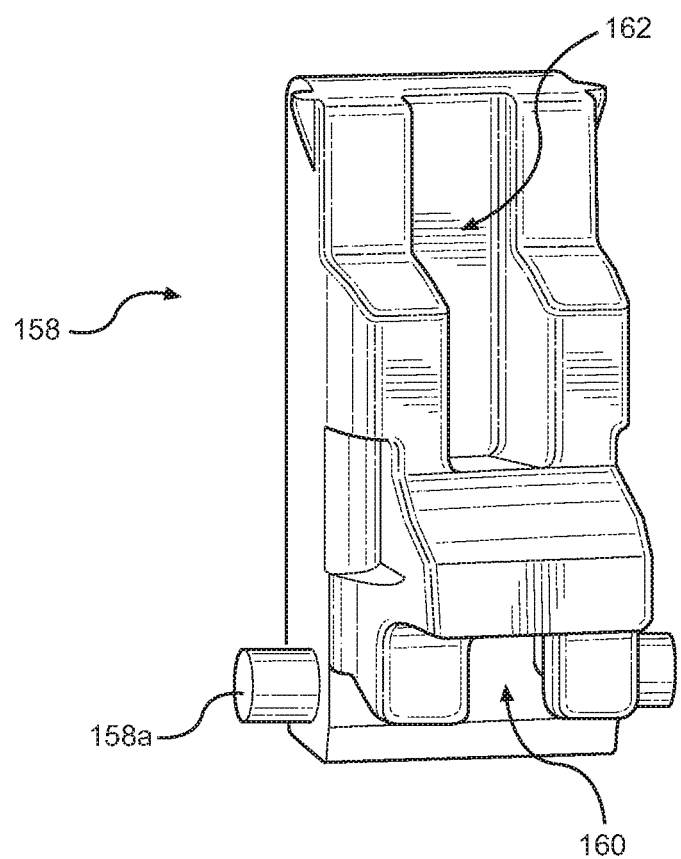
FIG. 30 is a detailed view of a pivot latch component of the range of motion hinge.

A movable, and preferably pivoting latch 158 is hingedly connected as by a latch pin 158a to a distal portion of the stop 114. The latch 158 has a pair of locks 160 and 162 for cooperating with the keys 134 of the hinge plate 110 and the keys 144 of the hinge plate 112, respectively (FIGS. 29 and 30). The latch 158 is pivoted or rotated away from the plates 110 and 112 to an unlatched position for making adjustments. The latch 158 is pivoted or rotated toward the plates 110 and 112 to position the locks 160 and 162 within the keys 134 and 144 to lock the position of the stop 114. Thus, extension movement of the knee is permitted between the setting of the extension stop 114 of the hinge 20 and the extension stop 40d of the strut member 30.

As best seen in FIG. 29, the latch 158 pivots or rotates as represented by the arrow P in directions that are non-radial and perpendicular to the plane of the leg struts 12a and 12b and the rotational movement ROM of the hinge 20 and the leg struts 12a and 12b. This advantageously provides a user-friendly structure that is easier to use than conventional structures and enables an increased surface area for improved frictional interface between the locks 160 and 162 of the latch 158 and the keys 134 of the hinge plate 110 and the keys 144 of the hinge plate 112.

The non-radial pivotal movement of the latch 158 and its cooperation with the position indicator 156 of the stop 114 (and similarly with respect to the stop 116) also advantageously enables the extension indicia 148a and the flexion indicia 148b to remain visible within the indicator windows 156a to visibly indicate the degree of extension and flexion to which the hinge 20 is adjusted.

To quickly set the flexion and the extension of the ROM hinge 20 (and the ROM hinge 22 if included), the brace 10 is initially positioned with the leg L of the patient and the brace 10 fully extended. The flexion stop 116 is set by pivoting the pivot latch thereof to the disengaged position and then sliding the stop 116 to the desired degree of flexion corresponding to the indicia 148b. When the flexion stop 116 is at the desired setting, the pivot latch is engaged to lock the position of the flexion stop 116. Thus, flexion movement of the knee is permitted between the setting of the stop 116 and the flexion stop 40c of the strut member 30.

The extension stop 114 is set to the desired extension angle in the same manner. That is, the extension stop 114 is set by pivoting the pivot latch 158 thereof to the disengaged position (the locks 160 and 162 disengaged) and then sliding the stop 114 to the desired degree of flexion corresponding to the indicia 148a. When the extension stop 114 is at the desired setting, the pivot latch 158 is engaged to lock the position of the extension stop 114 by engaging the locks 160 and 162 with the keys 134 and 144 of the plates 110 and 112 to lock the position of the stop 114. Thus, extension movement of the knee is permitted between the setting of the stop 114 and the extension stop 40d of the strut member 30.

The lock lever 118 is a slide lever of molded plastic construction and preferably includes a pair of spaced apart metal pins 170 located at a distal end thereof. The distal end of the lock lever 118 and the pins 170 are configured so that the pins 170 may be received by the teeth 40b of the uppermost crown portion of the upper end 40 of the strut member 30. The lock lever 118 is slidably positioned on the interior of the hinge plate 112 by the mount 120 to enable the lock lever 118 to be selectively positioned so that the pins 170 are engaged with the teeth 40b or not engaged with the teeth 40b. Engagement of the teeth 40b with the pins 170 serves to lock the brace 10 at a desired locked position. The teeth 40 are coordinated with the indicia 44 on the strut member 30 to facilitate locking of the brace at preset extension angles, such as at 0°, 15°, 30°, 45°. The lock lever 118 may be withdrawn out of engagement with the teeth 40b by retracting the lever 118 into the notch 100b of the strut member 100.

To quickly set the drop lock adjustment of the ROM hinge 20 (and the ROM hinge 22) to a preset extension position, the indicia 148 on the plate 112 is aligned with the desired drop lock preset indicia 44 (0°, 15°, 30°, 45°) located on the strut member 30. The lock member 118 is then pushed to slidably engage the pins 170 with the teeth 40b of the uppermost crown portion of the upper end 40 of the strut member 30 to lock the desired preset extension position. To unlock, the lever 118 is withdrawn by sliding the lever away from the hinge to withdraw the pins 170 from the teeth 40b.

The knee brace 10 according to the disclosure will therefore be understood to provide an adjustable knee braces of improved construction. The knee brace telescoping strut structure of the brace enables quick and easy incremental adjustment of the lengths of strut portions of the brace to enable custom fitting of the brace to a variety of leg lengths. The range of motion hinge structure is of improved construction and advantageously facilitates quick and easy adjustment of flexion and extension settings of the knee brace, and locking of the knee brace.

The foregoing description of preferred embodiments for this disclosure have been presented for purposes of illustration and description. They are not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An adjustable knee brace for fitting a variety of leg sizes and adjustable to limit flexion or extension motion of a knee, the brace comprising:
   a pair of telescoping struts, each strut comprising a strut member, a receiver configured to receive the strut member and telescopically positionable relative to the strut member, and a latch assembly mounted on the receiver, the latch assembly comprising:
      a cam base having a cam surface adjacent a portion of the strut member received by the receiver, and
      a pivot member pivotable mounted on the receiver for pivotal movement relative to the cam base, the pivot member having an engagement surface positioned to contact the cam surface of the cam base such that pivoting of the pivot member in one direction relative to the cam base selectively bears the cam base towards the strut member to apply a frictional force to lock the strut member and the receiver against relative telescoping movement, and pivoting the pivot member in an opposite direction removes the frictional force to unlock the strut member and the receiver and enable relative telescoping movement; and
   a range of motion hinge operatively associated with both of the telescoping struts, the range of motion hinge comprising:
      a pair of mating hinge plates connected to each of the strut members, each hinge plate having a semi-circular peripheral edge defining a plurality of uniformly spaced apart keys, the hinge plates being facing and aligned so that the peripheral edges are aligned and the keys of each hinge plate are aligned to define a first key set and a second key set,
      a flexion range of motion stop movably positionable relative to a first portion of the aligned semi-circular peripheral edges of the hinge plates, the flexion range of motion stop including a movable latch having teeth, wherein the movable latch is movable away from the first key set to an unlocked position in which the flexion range of motion stop is movable relative to the first key set, and the movable latch is movable toward and into engagement with the first key set to a locked position in which the flexion range of motion stop is not movable relative to the first key set, the hinge plate being movable within a first plane and the movable latch is movable within a second plane perpendicular to the first plane, and
      an extension range of motion stop movably positionable relative to a second portion of the aligned semi-circular peripheral edges of the hinge plates, the extension range of motion stop including a movable latch having teeth, wherein the movable latch is movable away from the second key set to an unlocked position in which the extension range of motion stop is movable relative to the second key set, and the movable latch is movable toward and into engagement with the second key set to a locked position in which the extension range of motion stop is not movable relative to the second key set, the hinge plate being movable within a first plane and the movable latch is movable within a second plane perpendicular to the first plane,
   wherein the flexion range of motion stop defines a limit of rotational movement of the range of motion hinge to limit flexion motion of the knee and the extension range of motion stop defines a limit of rotational movement of the range of motion hinge to limit extension motion of the knee.

2. The knee brace of claim 1, further comprising a sliding lock lever slidingly mounted to the range of motion hinge and slidingly engageable with one of the struts to lock the hinge at a desired orientation.

3. The knee brace of claim 2, wherein the strut with which the lock lever is engageable includes peripheral teeth engaged by the lock lever.

4. The knee brace of claim 1, further comprising a pad mount connected to at least one of the strut members opposite the latch assembly with a wedge shaped spacer located between the pad mount and the strut member, wherein the wedge shaped spacer may be provided in different slopes and thickness to enable a more custom fit to a leg of a patient wearing the brace.

5. An adjustable knee brace for fitting a variety of leg sizes and adjustable to limit flexion or extension motion of a knee, the brace comprising:

a telescoping strut, comprising a strut member, a receiver configured to receive the strut member and telescopically positionable relative to the strut member, and a latch assembly mounted on the receiver, the latch assembly comprising a cam base having a cam surface adjacent a portion of the strut member received by the receiver and a pivot member pivotable mounted on the receiver for pivotal movement relative to the cam base, the pivot member having an engagement surface positioned to contact the cam surface of the cam base such that pivoting of the pivot member in one direction relative to the cam base selectively bears the cam base towards the strut member to apply a frictional force to lock the strut member and the receiver against relative telescoping movement, and pivoting the pivot member in an opposite direction removes the frictional force to unlock the strut member and the receiver and enable relative telescoping movement; and a range of motion hinge operatively associated with the telescoping strut, the range of motion hinge comprising a hinge plate connected to the strut member and having a semi-circular peripheral edge defining a plurality of uniformly spaced apart keys, a range of motion stop movably positionable relative to the semi-circular peripheral edge, the range of motion stop including a movable latch having teeth, wherein the movable latch is movable away from the keys to an unlocked position in which the stop is movable relative to the keys, and the movable latch is movable toward and into engagement with the keys to a locked position in which the range of motion stop is not movable relative to the keys, wherein the movable latch is movable by pivoting away from engagement with the keys and by pivoting into engagement with the keys, wherein the hinge plate is movable within a first plane and the movable latch is movable within a second plane perpendicular to the first plane, and wherein the range of motion stop defines a limit of rotational movement of the range of motion hinge to limit extension or flexion motion of the knee.

6. The knee brace of claim 1, wherein the cam surface comprises an alternating series of ramped and flat surfaces and the engagement surface comprises a negative contour of the cam surface.

7. A telescoping strut for an adjustable knee brace, comprising:

a strut member;

a receiver configured to receive the strut member and telescopically positionable relative to the strut member; and a latch assembly mounted on the receiver, the latch assembly comprising a cam base having a cam surface comprising an alternating series of ramped and flat surfaces adjacent a portion of the strut member received by the receiver and a pivot member pivotable mounted on the receiver for pivotal movement relative to the cam base, the pivot member having an engagement surface comprising a negative contour of the cam surface positioned to contact the cam surface of the cam base such that pivoting of the pivot member in one direction relative to the cam base selectively bears the cam base towards the strut member to apply a frictional force to lock the strut member and the receiver against relative telescoping movement, and pivoting the pivot member in an opposite direction removes the frictional force to unlock the strut member and the receiver and enable relative telescoping movement.

8. The telescoping strut of claim 7, further comprising a pad mount connected to the strut member opposite the latch assembly with a wedge shaped spacer located between the pad mount and the strut member, wherein the wedge shaped spacer may be provided in different slopes and thickness to enable a more custom fit to a leg of a patient wearing the brace.

9. An adjustable range of motion hinge for a knee brace limit flexion or extension motion of a knee, the hinge comprising:

a hinge plate having a semi-circular peripheral edge defining a plurality of uniformly spaced apart keys; and a range of motion stop movably positionable relative to the semi-circular peripheral edge of the hinge plate, the range of motion stop including a movable latch having teeth, wherein the movable latch is movable away from the keys to an unlocked position in which the stop is movable relative to the keys, and the movable latch is movable toward and into engagement with the keys to a locked position in which the range of motion stop is not movable relative to the keys, wherein the movable latch is movable by pivoting away from engagement with the keys and by pivoting into engagement with the keys, wherein the hinge plate is movable within a first plane and the movable latch is movable within a second plane perpendicular to the first plane, and wherein the range of motion stop defines a limit of rotational movement of the range of motion hinge to limit extension or flexion motion of the knee.

* * * * *